United States Patent [19]
Ashton et al.

[11] Patent Number: 5,187,179
[45] Date of Patent: Feb. 16, 1993

[54] ANGIOTENSIN II ANTAGONISTS INCORPORATING A SUBSTITUTED IMIDAZO [1,2-B][1,2,4]TRIAZOLE

[75] Inventors: Wallace T. Ashton, Clark; Steven M. Hutchins, Iselin; Malcolm MacCoss, Freehold, all of N.J.

[73] Assignee: Merck & Co., Inc., Rahway, N.J.

[21] Appl. No.: 673,630

[22] Filed: Mar. 22, 1991

[51] Int. Cl.$^5$ .................. A61K 31/41; C07D 249/08; C07D 279/10; C07D 413/10

[52] U.S. Cl. .................. 514/383; 514/228.5; 514/234.5; 514/255; 514/341; 514/367; 514/371; 514/384; 544/57; 544/58.6; 544/60; 544/111; 544/113; 544/114; 544/337; 544/364; 548/252; 548/262.2; 548/262.4; 548/255

[58] Field of Search ............... 548/252, 264, 267, 268, 548/183, 262.4, 262; 546/185, 278; 514/228.5, 255, 341, 369, 371, 234.5, 383, 384, 367; 544/57, 58.6, 60, 111, 113, 114, 337, 368

[56] References Cited

U.S. PATENT DOCUMENTS 4,880,804  11/1989  Carini et al. .................. 514/234.5

FOREIGN PATENT DOCUMENTS

| | | |
|---|---|---|
| 58696/90 | 7/1989 | Australia . |
| 0253310 | 7/1987 | European Pat. Off. . |
| 0260613 | 9/1987 | European Pat. Off. . |
| 0324377 | 1/1989 | European Pat. Off. . |
| 0323841 | 7/1989 | European Pat. Off. . |
| 0392317 | 4/1990 | European Pat. Off. . |
| 0399731 | 5/1990 | European Pat. Off. . |
| 0399732 | 5/1990 | European Pat. Off. . |
| 0400974 | 5/1990 | European Pat. Off. . |
| 0403158 | 6/1990 | European Pat. Off. . |
| 0403159 | 6/1990 | European Pat. Off. . |
| 0411766 | 6/1990 | European Pat. Off. . |
| 409332 | 7/1990 | European Pat. Off. . |
| 0412594 | 7/1990 | European Pat. Off. . |
| 0415886 | 8/1990 | European Pat. Off. . |
| 0419048 | 8/1990 | European Pat. Off. . |
| 0429257 | 11/1990 | European Pat. Off. . |
| 8911855 | 5/1989 | United Kingdom . |
| 9005843 | 3/1990 | United Kingdom . |

OTHER PUBLICATIONS

Molina et al, Chemical Abstract, 1989, 112(21)

*Primary Examiner*—Nicholas S. Rizzo
*Assistant Examiner*—Y. N. Gupta
*Attorney, Agent, or Firm*—Valerie J. Camara; Joseph F. DiPrima; William H. Nicholson

[57] ABSTRACT

There are disclosed substituted imidazo[1,2-b][1,2,4]triazole derivatives of Formula I which are useful as angiotensin II antagonists.

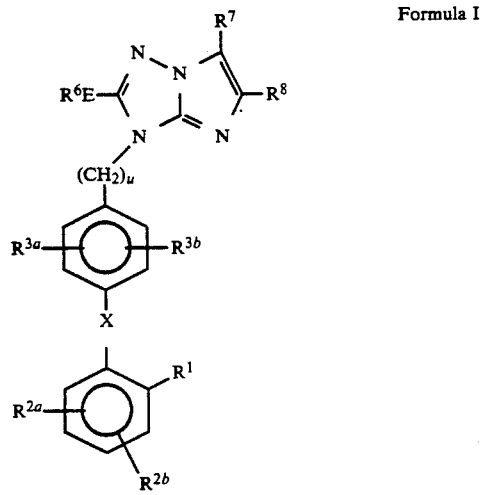

Formula I

12 Claims, No Drawings

ANGIOTENSIN II ANTAGONISTS INCORPORATING A SUBSTITUTED IMIDAZO [1,2-B][1,2,4]TRIAZOLE

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in this application have been identified in any U.S. Patent, European Applications or articles. The substituted imidazoles referred to above have been disclosed in patents to DuPont (EPO 253,310 and EPO 324,377) focusing on the design of Angiotensin II Antagonists.

BRIEF DESCRIPTION OF THE INVENTION

The compounds of formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure are also described.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

DETAILED DESCRIPTION OF THE INVENTION

The compounds of this invention have the general formula (I) and their pharmaceutically acceptable salts

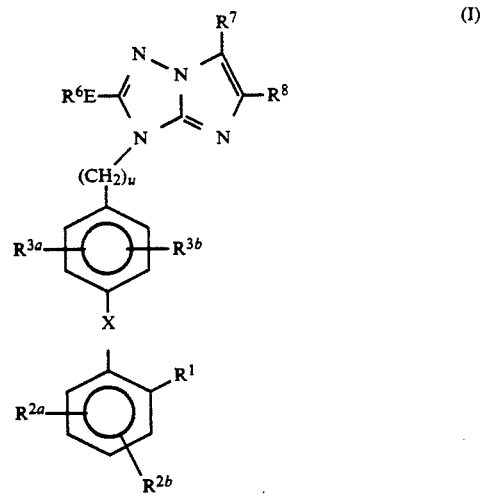

wherein:

$R^1$ is
- (a) $-CO_2R^5$,
- (b) $-SO_3R^5$,
- (c) $-NHSO_2CF_3$,
- (d) $-PO(OR^5)_2$,
- (e) $-SO_2-NH-R^9$,
- (f) $-CONHOR^5$,
- (g) $-SO_2NH$-heteroaryl, wherein heteroaryl is an unsubstituted, monosubstituted or disubstituted 5- or 6-membered aromatic ring which can contain from 1 to 3 heteroatoms selected from the group consisting of O, N and S and wherein the substituents are members selected from the group consisting of $-OH$, $-SH$, $(C_1-C_4)$-alkyl, $(C_1-C_4)$-alkoxy, $-CF_3$, Cl, Br, F, I, $-NO_2$, $-CO_2H$, $-CO_2-(C_1-C_4)$-alkyl, $-NH_2$, $-NH[(C_1-C_4)$-alkyl] or $-N[(C_1-C_4)$-alkyl]$_2$,
- (h) $-CH_2SO_2NH$-heteroaryl,
- (i) $-SO_2NHCOR^{23}$,
- (j) $-CH_2SO_2NHCOR^{23}$,
- (k) $-CONHSO_2R^{23}$,
- (l) $-CH_2CONHSO_2R^{23}$,
- (m) $-NHSO_2NHCOR^{23}$,
- (n) $-NHCONHSO_2R^{23}$,

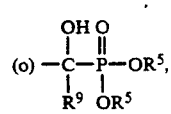

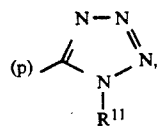

-continued

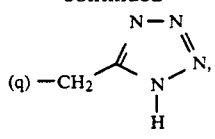

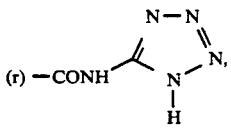

(s) —CONHNHSO$_2$CF$_3$,

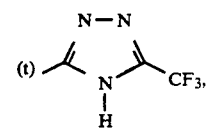

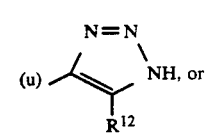

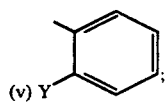

Y is
(1) —CO$_2$R$^4$,
(2) —SO$_3$R$^5$,
(3) —NHSO$_2$CF$_3$,
(4) —PO(OR$^5$)$_2$,
(5) —SO$_2$—NH—R$^9$, or
(6) 1H-tetrazol-5-yl;

R$^{2a}$ and R$^{2b}$ are each independently:
(a) hydrogen,
(b) Cl, Br, I, F,
(c) NO$_2$,
(d) NH$_2$,
(e) (C$_1$-C$_4$)-alkylamino,
(f) —SO$_2$NHR$^9$,
(g) CF$_3$,
(h) (C$_1$-C$_4$)-alkyl,
(i) (C$_1$-C$_4$)-alkoxy, or
(j) when R$^{2a}$ and R$^{2b}$ are on adjacent carbons, they can be bonded together to form a phenyl ring;

R$^{3a}$ is
(a) H,
(b) Cl, Br, I, F,
(c) (C$_1$-C$_6$)-alkyl,
(d) (C$_1$-C$_6$)-alkoxy, or
(e) (C$_1$-C$_6$)-alkoxy-(C$_1$-C$_4$)-alkyl;

R$^{3b}$ is
(a) H,
(b) Cl, Br, I, F,
(c) NO$_2$,
(d) (C$_1$-C$_6$)-alkyl,
(e) (C$_1$-C$_5$)-alkylcarbonyloxy,
(f) (C$_3$-C$_6$)-cycloalkyl,
(g) (C$_1$-C$_6$)-alkoxy,
(h) —NHSO$_2$R$^4$,
(i) hydroxy-(C$_1$-C$_4$)-alkyl,
(j) aryl-(C$_1$-C$_4$)-alkyl,
(k) (C$_1$-C$_4$)-alkylthio,
(l) (C$_1$-C$_4$)-alkylsulfinyl,
(m) (C$_1$-C$_4$)-alkylsulfonyl,
(n) NH$_2$,
(o) (C$_1$-C$_4$)-alkylamino,
(p) di[(C$_1$-C$_4$)-alkyl]amino,
(q) CF$_3$,
(r) —SO$_2$—NHR$^9$,
(s) aryl, wherein aryl is phenyl or naphthyl unsubstituted or substituted with one or two substituents selected from the group consisting of: Cl, Br, I, F (C$_1$-C$_4$)-alkyl, (C$_1$-C$_4$)-alkoxy, NO$_2$, CF$_3$, (C$_1$-C$_4$)-alkylthio, OH or NH$_2$,
(t) furyl, or
(u) when R$^{3a}$ and R$^{3b}$ are on adjacent carbons, they can be bonded together to form a phenyl ring;

R$^4$ is H, (C$_1$-C$_6$)-alkyl, aryl or —CH$_2$-aryl;
R$^{4a}$ is (C$_1$-C$_6$)-alkyl, aryl or —CH$_2$-aryl;
R$^5$ is H or —CH(R$^4$)—O—CO—R$^{4a}$;
E is a single bond, —NR$^{13}$(CH$_2$)$_s$—, —S(O)$_x$(CH$_2$)$_s$— where x is 0 to 2 and s is 0 to 5, —CH(OH)—, —O(CH$_2$)$_s$— or —CO—;

R$^6$ is
(a) aryl, unsubstituted or substituted with 1 or 2 substituents selected from the group consisting of: Cl, Br, I, F, —O—(C$_1$-C$_4$)-alkyl, (C$_1$-C$_4$)-alkyl, —NO$_2$, —CF$_3$, —SO$_2$NR$^9$R$^{10}$, —S—(C$_1$-C$_4$)-alkyl, —OH, —NH$_2$, (C$_3$-C$_7$)-cycloalkyl, (C$_3$-C$_{10}$)-alkenyl,
(b) (C$_1$-C$_6$)-alkyl, (C$_2$-C$_6$)-alkenyl or (C$_2$-C$_6$)-alkynyl each of which can be unsubstituted or substituted with one or more substituents selected from the group consisting of: aryl, C$_3$-C$_7$-cycloalkyl, Cl, Br, I, F, —OH, —O—C$_1$-C$_4$-alkyl, —NH$_2$, —NH[(C$_1$-C$_4$)-alkyl], —N[(C$_1$-C$_4$)-alkyl]$_2$, —NH—SO$_2$R$^4$, —COOR$^4$, —SO$_2$NHR$^9$, or —S—(C$_1$-C$_4$)-alkyl,
(c) an unsubstituted, monosubstituted or disubstituted aromatic 5- or 6-membered ring which can contain one or two heteroatoms selected from the group consisting of N, O, S, and wherein the substituents are members selected from the group consisting of: —OH, —SH, (C$_1$-C$_4$)-alkyl, (C$_1$-C$_4$)-alkyloxy, —CF$_3$, Cl, Br, I, F, or NO$_2$,
(d) mono-, di-, tri- or polyfluoro-(C$_1$-C$_5$)-alkyl,
(e) (C$_3$-C$_7$)-cycloalkyl, unsubstituted or substituted with one or more substituents selected from the group consisting of: (C$_1$-C$_4$)-alkyl, O-(C$_1$-C$_4$)-alkyl, S-(C$_1$-C$_4$)-alkyl, OH, perfluoro-(C$_1$-C$_4$)-alkyl, Cl, Br, F or I, or
(f) (C$_3$-C$_7$)-cycloalkyl-(C$_1$-C$_3$)-alkyl wherein the cycloalkyl is substituted as in (e) above;

R$^7$ and R$^8$ are independently:
(a) H,
(b) (C$_1$-C$_{10}$)-alkyl, unsubstituted or substituted (C$_1$-C$_{10}$)-alkyl in which one or more substituent(s) is selected from the group consisting of:
(1) I, Br, Cl, F,
(2) hydroxy,
(3) (C$_1$-C$_{10}$)-alkoxy,
(4) (C$_1$-C$_5$)-alkoxycarbonyl,
(5) (C$_1$-C$_4$)-alkylcarbonyloxy,
(6) (C$_3$-C$_8$)-cycloalkyl,
(7) aryl,
(8) substituted aryl in which the substituents are V$_1$, V$_2$, V$_3$, V$_4$ and V$_5$,
(9) (C$_1$-C$_{10}$)-alkyl-S(O)$_p$ in which p is 0 to 2,
(10) (C$_3$-C$_8$)-cycloalkyl-S(O)$_p$,

(11) phenyl-S(O)$_p$,
(12) substituted phenyl-S(O)$_p$ in which the substituents are $V_1$-$V_5$,
(13) oxo,
(14) carboxy,
(15) NR$^9$R$^9$,
(16) CONH-(C$_1$-C$_5$)-alkyl,
(17) CON[(C$_1$-C$_5$)-alkyl]$_2$, or
(18) cyano, (c) (C$_2$-C$_{10}$)-alkenyl,
(d) (C$_2$-C$_{10}$)-alkynyl,
(e) (C$_3$-C$_8$)-cycloalkyl,
(f) substituted (C$_3$-C$_8$)-cycloalkyl or substituted (C$_3$-C$_8$)-cycloalkyl-C$_1$-C$_4$-alkyl having one or more substituents selected from the group:
(1) Cl, Br, F, I,
(2) hydroxy,
(3) (C$_1$-C$_6$)-alkyl,
(4) (C$_1$-C$_6$)-alkoxy,
(5) (C$_1$-C$_4$)-alkylcarbonyloxy,
(6) (C$_1$-C$_5$)-alkoxycarbonyl,
(7) carboxy,
(8) oxo,
(9) (C$_1$-C$_5$)-alkylaminocarbonyl,
(10) di[(C$_1$-C$_5$)-alkylaminocarbonyl,
(11) (C$_1$-C$_4$)-alkylcarbonyl,
(12) aryl, or
(13) substituted aryl in which the substituents are $V_1$, $V_2$, $V_3$, $V_4$ and $V_5$,
(g) aryl,
(h) substituted aryl in which the substituents are $V_1$, $V_2$, $V_3$, $V_4$ and $V_5$,
(i) aryl-(CH$_2$)$_r$-(Q)$_c$-(CH$_2$)$_r$-,
(j) substituted aryl-(CH$_2$)$_r$-(Q)$_c$-(CH$_2$)$_r$- in which the aryl group is substituted with $V_1$, $V_2$, $V_3$, $V_4$ and $V_5$,
(k) a heterocyclic moiety selected from the group consisting of:

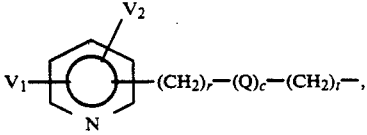

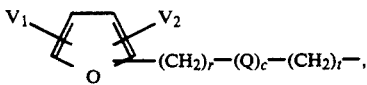

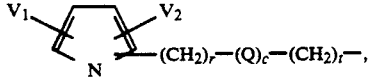

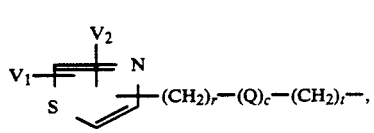

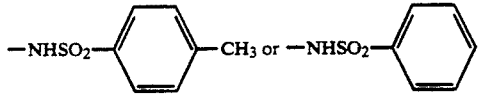

(l) Cl, Br, I, F,
(m) nitro,
(n) nitroso,
(o) NR$^9$R$^{10}$,
(p) NR$^4$COR$^9$,
(q) NR$^4$CO$_2$R$^9$,
(r) NR$^4$CONR$^9$R$^{10}$,
(s) NR$^4$CON(CH$_2$CH$_2$)$_2$G,
(t) NHSO$_2$CF$_3$,
(u) CO$_2$R$^4$,
(v) CN,
(w) 1H-tetrazol-5-yl,
(x) O-(C$_1$-C$_4$)-alkyl, or
(y) S(O)$_p$-(C$_1$-C$_4$)-alkyl;

G is O, S(O)$_p$, or NR$^9$;
R$^9$ is H, (C$_1$-C$_5$)-alkyl, aryl or —CH$_2$-aryl;
R$^{10}$ is H, (C$_1$-C$_4$)-alkyl, or R$^9$ and R$^{10}$ together can be —(CH$_2$)$_m$—, where m is 3-6;
R$^{11}$ is H, (C$_1$-C$_6$)-alkyl, (C$_2$-C$_4$)-alkenyl, (C$_1$-C$_4$)-alkoxy-(C$_1$-C$_4$)-alkyl, or —CH$_2$—C$_6$H$_4$R$^{20}$;
R$^{12}$ is —CN, —NO$_2$ or —CO$_2$R$^4$;
R$^{13}$ is H, (C$_1$-C$_4$)-acyl, (C$_1$-C$_6$)-alkyl, allyl, (C$_3$-C$_6$)-cycloalkyl, phenyl or benzyl;
R$^{14}$ is H, (C$_1$-C$_8$)-alkyl, (C$_1$-C$_8$)-perfluoroalkyl, (C$_3$-C$_6$)-cycloalkyl, phenyl or benzyl;
R$^{15}$ is H, (C$_1$-C$_6$)-alkyl or hydroxy;
R$^{16}$ is H, (C$_1$-C$_6$)-alkyl, (C$_3$-C$_6$)-cycloalkyl, phenyl or benzyl;
R$^{17}$ is —NR$^9$R$^{10}$, —OR$^{10}$, —NHCONH$_2$, —NHCSNH$_2$, —NHSO$_2$CF$_3$, —NHSO$_2$—⟨phenyl⟩—CH$_3$ or —NHSO$_2$—⟨phenyl⟩;

R$^{18}$ and R$^{19}$ are independently (C$_1$-C$_4$)-alkyl or taken together are —(CH$_2$)$_q$-where q is 2 or 3;
R$^{20}$ is H, —NO$_2$, —NH$_2$, —OH or —OCH$_3$;
R$^{23}$ is
  (a) aryl,
  (b) heteroaryl,
  (c) (C$_3$-C$_7$)-cycloalkyl,
  (d) (C$_1$-C$_4$)-alkyl, unsubstituted or substituted with a substituent selected from the group consisting of: aryl, heteroaryl, —OH, —SH, (C$_1$-C$_4$)-alkyl, —O[(C$_1$-C$_4$)-alkyl], S(C$_1$-C$_4$)-alkyl, —CF$_3$, Cl, Br, F, I, —NO$_2$, —CO$_2$H, —CO$_2$—(C$_1$-C$_4$)-alkyl, —NH$_2$, —NH(C$_1$-C$_4$)-alkyl, —N[(-C$_1$-C$_4$)-alkyl]$_2$, —N(CH$_2$CH$_2$)$_2$L, —PO$_3$H, —PO(OH)(O—(C$_1$-C$_4$)-alkyl);
L is a single bond, CH$_2$, O, S(O)$_p$, or NR$^9$;
X is
  (a) a single bond,
  (b) —CO—,
  (c) —O—,
  (d) —S—,
  (e) —N—, R$^{13}$
  (f) —CON—, R$^{15}$
  (g) —NCO—, R$^{15}$
  (h) —OCH$_2$—,
  (i) —CH$_2$O—
  (j) —SCH$_2$—,
  (k) —CH$_2$S—,
  (l) —NHC(R$^9$)(R$^{10}$)—,
  (m) —NR$^9$SO$_2$—,
  (n) —SO$_2$NR$^9$—,
  (o) —C(R$^9$)(R$^{10}$)NH—,
  (p) —CH=CH—,
  (q) —CF=CF—,
  (r) —CH=CF—,
  (s) —CF=CH—, (t) —CH₂CH₂—,
(u) —CF₂CF₂—, (v) 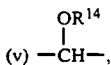

(w) 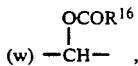

(x) 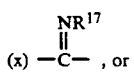, or (y) 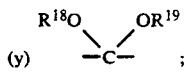;

Q is —C(O)—, —S—, —O— or —NR⁴;
c is 0 or 1;
r and t are 0 to 2;
V₁, V₂, V₃, V₄ and V₅ are each independently selected from:
  (a) H,
  (b) (C₁–C₅)-alkoxy,
  (c) (C₁–C₅)-alkyl,
  (d) hydroxy,
  (e) (C₁–C₅)-alkyl-S(O)$_p$,
  (f) —CN,
  (g) —NO₂,
  (h) —NR⁹R¹⁰,
  (i) (C₁–C₅)-alkyl-CONR⁹R¹⁰,
  (j) —CONR⁹R¹⁰,
  (k) —CO₂R⁹,
  (l) (C₁–C₅)-alkyl-carbonyl,
  (m) CF₃,
  (n) I, Br, Cl, F,
  (o) hydroxy-(C₁–C₄)-alkyl-,
  (p) carboxy-(C₁–C₄)-alkyl-,
  (q) -1H-tetrazol-5-yl,
  (r) —NH—SO₂CF₃,
  (s) aryl,
  (t) (C₁–C₅)-alkyl-CO₂R⁹,
  (u) aryloxy,
  (v) aryl-(C₁–C₃)-alkoxy,
  (w) aryl-(C₁–C₃)-alkyl,
  (x) carboxyphenyl,
  (y) heteroaryl,
  (z) 2-oxazolin-2-yl, unsubstituted or substituted with one or more (C₁–C₄)-alkyl substituents,
  (aa) —(CH₂)$_r$OCOR⁹,
  (bb) —(CH₂)$_r$OCONR⁹R¹⁰,
  (cc) —(CH₂)$_t$NR⁴COR⁹,
  (dd) —(CH₂)$_t$NR⁴CO₂R⁹,
  (ee) —(CH₂)$_t$NR⁴CONR⁹R¹⁰,
  (ff) —(CH₂)$_t$NR⁴CON(CH₂CH₂)₂G,
  (gg) —(CH₂)$_r$OCON(CH₂CH₂)₂G,
  (hh) —N(CH₂CH₂)₂G,
  (ii) —(C₁–C₅)-alkyl-CON(CH₂CH₂)₂G, or
  (jj) —CON(CH₂CH₂)G;
G is O, S(O)$_p$ or NR⁹;
u is 1 or 2; and
Z is O, NR¹³ or S.

One embodiment of the invention are those compounds of Formula I wherein:
R¹ is
  (a) —CO₂H,
  (b) -1H-tetrazol-5-yl,
  (c) —NHSO₂CF₃,
  (d) —CONHSO₂R²³, or
  (e) —SO₂NH-heteroaryl, wherein heteroaryl is an unsubstituted, monosubstituted or disubstituted 5- or 6-membered aromatic ring which can contain from 1 to 3 heteroatoms selected from the group consisting of O, N and S and wherein the substituents are members selected from the group consisting of: —OH, —SH, (C₁–C₄)-alkyl, (C₁–C₄)-alkoxy, —CF₃, Cl, Br, F, I, —NO₂, —CO₂H, —CO₂–(C₁–C₄)-alkyl, —NH₂, —NH[(C₁–C₄)-alkyl] or —N[(C₁–C₄)-alkyl]₂;
R²ᵃ is H;
R²ᵇ is:
  (a) hydrogen,
  (b) Cl, F,
  (c) CF₃,
  (d) (C₁–C₄)-alkyl, or
  (e) (C₁–C₄)-alkoxy;
R³ᵃ is H;
R³ᵇ is
  (a) H,
  (b) Cl, F,
  (c) (C₁–C₄)-alkyl,
  (d) CF₃,
  (e) (C₃–C₆)-cycloalkyl, or
  (f) (C₁–C₄)-alkoxy;
R⁴ is H, (C₁–C₆)-alkyl, aryl or —CH₂-aryl;
R⁴ᵃ is (C₁–C₆)-alkyl, aryl or —CH₂-aryl;
R⁵ is H or —CH(R⁴)-O-CO-R⁴ᵃ;
E is a single bond or —S—;
R⁶ is
  (a) (C₁–C₆)-alkyl, (C₂–C₆)-alkenyl or (C₂–C₆)-alkynyl each of which can be unsubstituted or substituted with one or more substituents selected from the group consisting of: aryl, (C₃–C₇)-cycloalkyl, Cl, Br, I, F, -OH, CF₃, —O—(C₁–C₄)-alkyl, —COOR⁴, or —S—(C₁–C₄)-alkyl,
  (b) (C₁–C₄)-perfluoroalkyl, or
  (c) (C₃–C₇)-cycloalkyl, unsubstituted or substituted with one or more substituents selected from the group consisting of: (C₁–C₄)-alkyl, O—(C₁–C₄)-alkyl, S—(C₁–C₄)-alkyl, OH, (C₁–C₄)-perfluoroalkyl, Cl, Br, F or I;
R⁷ and R⁸ are independently:
  (a) H,
  (b) (C₁–C₁₀)-alkyl, unsubstituted or substituted (C₁–C₁₀)-alkyl in which one or more substituent(s) is selected from the group consisting of:
    (1) hydroxy,
    (2) (C₁–C₆)-alkoxy,
    (3) (C₁–C₅)-alkoxycarbonyl,
    (4) (C₁–C₄)-alkylcarbonyloxy,
    (5) (C₃–C₈)-cycloalkyl,
    (6) phenyl,
    (7) substituted phenyl in which the substituents are V₁, V₂, V₃, V₄ and V₅,
    (8) (C₁–C₆)-alkyl-S(O)$_p$ in which p is 0 to 2,
    (9) (C₃–C₈)-cycloalkyl-S(O)$_p$,
    (10) phenyl-S(O)$_p$,
    (11) substituted phenyl-S(O)$_p$ in which the substituents are V₁-V₅,
    (12) oxo, or
    (13) carboxy;
  (c) (C₂–C₁₀)-alkenyl,
  (d) (C₂–C₁₀)-alkynyl,
  (e) (C₃–C₈)-cycloalkyl, (f) substituted ($C_3$-$C_8$)-cycloalkyl or substituted ($C_3$-$C_8$)-cycloalkyl-$C_1$-$C_4$-alkyl having one or more substituents selected from the group:
  (1) Cl, Br, F, I,
  (2) hydroxy,
  (3) ($C_1$-$C_6$)-alkyl,
  (4) ($C_1$-$C_6$)-alkoxy,
  (5) ($C_1$-$C_4$)-alkylcarbonyloxy,
  (6) ($C_1$-$C_5$)-alkoxycarbonyl,
  (7) carboxy,
  (8) oxo,
  (9) aryl, or
  (10) substituted aryl in which the substituents are $V_1$, $V_2$, $V_3$, $V_4$ and $V_5$,
(g) aryl,
(h) substituted aryl in which the substituents are $V_1$, $V_2$, $V_3$, $V_4$ and $V_5$,
(i) aryl—$(CH_2)_r$—$(Q)_c$—$(CH_2)_t$—,
(j) substituted aryl—$(CH_2)_r$—$(Q)_c$—$(CH_2)_t$— in which the aryl group is substituted with $V_1$, $V_2$, $V_3$, $V_4$ and $V_5$,
(k) a heterocyclic moiety selected from the group consisting of:

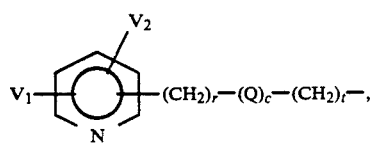

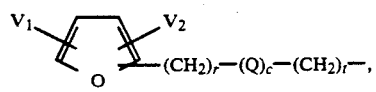

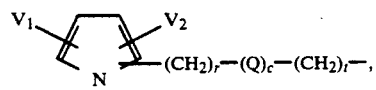

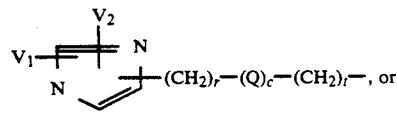

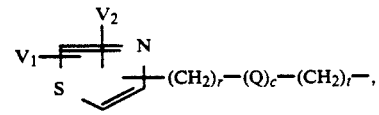

(l) Cl, Br, I, F,
(m) $CO_2R^4$, or
(n) ($C_1$-$C_{10}$)-perfluoroalkyl;

$R^9$ is H, ($C_1$-$C_5$)-alkyl, aryl or $CH_2$-aryl;
$R^{10}$ is H, ($C_1$-$C_4$)-alkyl, or $R^9$ and $R^{10}$ together can be —$(CH_2)_m$—, where m is 3-6;
$R^{11}$ is H, ($C_1$-$C_6$)-alkyl, ($C_2$-$C_4$)-alkenyl, ($C_1$-$C_4$)-alkoxy-($C_1$-$C_4$)-alkyl, or —$CH_2$—$C_6H_4R^{20}$;
$R^{12}$ is —CN, —$NO_2$ or —$CO_2R^4$;
$R^{13}$ is H, ($C_1$-$C_4$)-acyl, ($C_1$-$C_6$)-alkyl, allyl, ($C_3$-$C_6$)-cycloalkyl, phenyl or benzyl;
$R^{14}$ is H, ($C_1$-$C_8$)-alkyl, ($C_1$-$C_8$)-perfluoroalkyl, ($C_3$-$C_6$)-cycloalkyl, phenyl or benzyl;
$R^{15}$ is H, ($C_1$-$C_6$)-alkyl or hydroxy;
$R^{16}$ is H, ($C_1$-$C_6$)-alkyl, ($C_3$-$C_6$)-cycloalkyl, phenyl or benzyl;
$R^{17}$ is —$NR^9R^{10}$, —$OR^{10}$, —$NHCONH_2$, —$NHCSNH_2$, —$NHSO_2CF_3$,

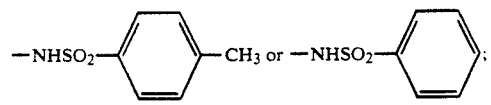

$R^{18}$ and $R^{19}$ are independently ($C_1$-$C_4$)-alkyl or taken together are —$(CH_2)_q$—where q is 2 or 3;
$R^{20}$ is H, —$NO_2$, —$NH_2$, —OH or —$OCH_3$;
$R^{23}$ is
  (a) aryl,
  (b) heteroaryl,
  (c) ($C_3$-$C_7$)-cycloalkyl,
  (d) ($C_1$-$C_4$)-alkyl, unsubstituted or substituted with a substituent selected from the group consisting of: aryl, heteroaryl, —OH, —SH, ($C_1$-$C_4$)-alkyl, —O[($C_1$-$C_4$)-alkyl], S($C_1$-$C_4$)-alkyl, —$CF_3$, Cl, Br, F, I, —$NO_2$, —$CO_2H$, —$CO_2$—($C_1$-$C_4$)-alkyl, —$NH_2$, —NH($C_1$-$C_4$)-alkyl, —N[($C_1$-$C_4$)-alkyl]$_2$, —N($CH_2CH_2$)$_2$L, —$PO_3H$, —PO(OH)(O—($C_1$-$C_4$)-alkyl);

L is a single bond, $CH_2$, O, $S(O)_p$, or $NR^9$;
X is
  (a) a single bond,
  (b) —C(O)—,
  (c) —NHC(O),
Q is —C(O)—, —S—, —O— or —$NR^4$;
c is 0 or 1;
r and t are 0 to 2;
$V_1$, $V_2$, $V_3$, $V_4$ and $V_5$ are each independently selected from:
  (a) H,
  (b) ($C_1$-$C_5$)-alkoxy,
  (c) ($C_1$-$C_5$)-alkyl,
  (d) hydroxy,
  (e) ($C_1$-$C_5$)-alkyl-$S(O)_p$,
  (f) —CN,
  (g) —$NO_2$,
  (h) —$NR^9R^{10}$,
  (i) ($C_1$-$C_5$)-alkyl-$CONR^9R^{10}$,
  (j) —$CONR^9R^{10}$,
  (k) —$CO_2R^9$,
  (l) $CF_3$,
  (m) I, Br, Cl, F,
  (n) hydroxy-($C_1$-$C_4$)-alkyl-,
  (o) —1H-tetrazol-5-yl,
  (p) —NH—$SO_2CF_3$,
  (q) aryl,
  (r) ($C_1$-$C_5$)-alkyl-$CO_2R^9$,
  (s) aryl-($C_1$-$C_3$)-alkyl,
  (t) heteroaryl,
  (u) 2-oxazolin-2-yl, unsubstituted or substituted with one or more ($C_1$-$C_4$)-alkyl substituents,
  (v) —$(CH_2)_uOCOR^9$, or
  (w) —$(CH_2)_uOCONR^9R^{10}$;
u is 1; and
Z is O, $NR^{13}$ or S.

The preferred compounds of this invention include:
2-Butyl-6-methyl-5-phenyl-3-[[2'-(5-tetrazolyl)-biphenyl-4-yl]methyl]-3H-imidazo[1,2-b][1,2,4]triazole
2-Butyl-5-phenyl-3-[[2'-(5-tetrazolyl)biphenyl-4-yl]methyl]-3H-imidazo[1,2-b][1,2,4]triazole
2-Butyl-5-methyl-3-[[2'-(5-tetrazolyl)biphenyl-4-yl]methyl]-3H-imidazo[1,2-b][1,2,4]triazole
2-Butyl-5-ethyl-3-[[2'-(5-tetrazolyl)biphenyl-4-yl]methyl]-3H-imidazo[1,2-b][1,2,4]triazole 2-Butyl-6-methyl-3-[[2'-(5-tetrazolyl)biphenyl-4-yl]-methyl]-3H-imidazo[1,2-b][1,2,4]triazole
2-Butyl-5,6-dimethyl-3-[[2'-(5-tetrazolyl)biphenyl-4-yl]methyl]-3H-imidazo[1,2-b][1,2,4]triazole
2-Butyl-5-methyl-6-phenyl-3-[[2'-(5-tetrazolyl)biphenyl-4-yl]methyl]-3H-imidazo[1,2-b][1,2,4]triazole
2-Butyl-6-phenyl-3-[[2'-(5-tetrazolyl)biphenyl-4-yl]methyl]-3H-imidazo[1,2-b][1,2,4]triazole
2-Butyl-3-[[2'-(5-tetrazolyl)biphenyl-4-yl]methyl]-3H-imidazo[1,2-b][1,2,4]triazole
2-Butyl-5-(4-methoxyphenyl)-6-methyl-3-[[2'-(5-tetrazolyl)biphenyl-4-yl]methyl]-3H-imidazo[1,2-b]-[1,2,4]triazole
2-Butyl-3-[[2'-(5-tetrazolyl)biphenyl-4-yl]methyl]-3H-imidazo[1,2-b][1,2,4]triazole-5-carboxylic acid
2-Butyl-6-methyl-3-[[2'-(5-tetrazolyl)biphenyl-4-yl]methyl]-3H-imidazo[1,2-b][1,2,4]triazole-5-carboxylic acid
2-Butyl-5-(2-carboxyphenyl)-6-methyl-3-[[2'-(5-tetrazolyl)biphenyl-4-yl]methyl]-3H-imidazo[1,2-b][1,2,4]triazole
5,6-Dimethyl-2-propyl-3-[[2'-(5-tetrazolyl)biphenyl-4-yl]methyl]-3H-imidazo[1,2-b][1,2,4]triazole
5-Phenyl-2-propyl-3-[[2'-(5-tetrazolyl)biphenyl-4-yl]methyl]-3H-imidazo[1,2-b][1,2,4]triazole
6-Methyl-5-phenyl-2-propyl-3-[[2'-(2'-(5-tetrazolyl)-biphenyl-4-yl]methyl]-3H-imidazo[1,2-b][1,2,4]triazole
6-Methyl-2-propyl-3-[[2'-(5-tetrazolyl)biphenyl-4-yl]methyl]-3H-imidazo[1,2-b][1,2,4]triazole-5-carboxylic acid
5,6-Dimethyl-2-ethyl-3-[[2'-(5-tetrazolyl)biphenyl-4-yl]methyl]-3H-imidazo[1,2-b][1,2,4]triazole
2-Ethyl-5-phenyl-3-[[2'-(5-tetrazolyl)biphenyl-4-yl]methyl]-3H-imidazo[1,2-b][1,2,4]triazole
2-Ethyl-6-methyl-5-phenyl-3-[[2'-(5-tetrazolyl)biphenyl-4yl]methyl]-3H-imidazo[1,2-b][1,2,4]triazole
2-Ethyl-6-methyl-3-[[2'-(5-tetrazolyl)biphenyl-4-yl]methyl]-3H-imidazo[1,2-b][1,2,4]triazole-5-carboxylic acid
3-[[2'-(N-Benzoylsulfamoyl)biphenyl-4-yl]methyl]-2-butyl-6-methyl-5-phenyl-3H-imidazo[1,2-b][1,2,4]triazole
3-[[2'-(N-Benzoylsulfamoyl)biphenyl-4-yl]methyl]-2-butyl-5,6-dimethyl-3H-imidazo[1,2-b][1,2,4]triazole
3-[[2'-(N-Benzoylsulfamoyl)biphenyl-4-yl]methyl]-6-methyl-5-phenyl-2-propyl-3H-imidazo[1,2-b][1,2,4]triazole
3-[[2'-(N-Benzoylsulfamoyl)biphenyl-4-yl]methyl]-2-ethyl-6-methyl-5-phenyl-3H-imidazo[1,2-b][1,2,4]triazole
2-Butyl-6-methyl-5-phenyl-3-[[2'-(trifluoromethanesulfonamido)biphenyl-4-yl]methyl]-3H-imidazo[1,2-b][1,2,4]triazole
6-Methyl-5-phenyl-2-propyl-3-[[2'-(trifluoromethanesulfonamido)biphenyl-4-yl]methyl]-3H-imidazo[1,2-b][1,2,4]triazole
2-Butyl-3-[(2'-carboxybiphenyl-4-yl)methyl]-5,6-dimethyl-3H-imidazo[1,2-b][1,2,4]triazole
6-Bromo-2-butyl-5-phenyl-3-[[2'-(5-tetrazolyl)-biphenyl-4-yl]methyl]-3H-imidazo[1,2-b][1,2,4]triazole
5-Benzyl-2-butyl-6-methyl-3-[[2'-(5-tetrazolyl)-biphenyl-4-yl]methyl]-3H-imidazo[1,2-b][1,2,4]triazole Abbreviations used in the schemes and examples are listed in Table 1.

TABLE 1

Reagents

| | |
|---|---|
| NBS | N-bromosuccinimide |
| AIBN | 2,2'-a obis(isobutyronitrile) |
| Et₃N | triethylamine |
| Ph₃P | triphenylphosphine |
| TFA | trifluoroacetic acid |
| TsOH | p-toluenesulfonic acid |
| NaOEt | sodium ethoxide |
| NaOAc | sodium acetate |
| PPA | polyphosphoric acid |
| MCPBA | m-chloroperoxybenzoic acid |
| PPE | polyphosphate ester |
| CDI | 1,1'-carbonyldiimidazole |
| DBU | 1,8-diazabicyclo[5.4.0]undec-7-ene |
| MeI | methyl iodide |
| Solvents: | |
| DMF | dimethylformamide |
| AcOH | acetic acid |
| EtOAc | ethyl acetate |
| THF | tetrahydrofuran |
| DMSO | dimethylsulfoxide |
| MeOH | methanol |
| EtOH | ethanol |
| Others: | |
| Ph | phenyl |
| FAB-MS | fast atom bombardment mass spectroscopy |
| Ar | aryl |
| Me | methyl |
| Et | ethyl |
| t-Bu | tert-butyl |
| cat. | catalytic |
| concd. | concentrated |

DETAILED DESCRIPTION OF THE INVENTION

Imidazo[1,2-b][1,2,4]triazoles have been the subject of limited synthetic studies to date. The parent heterocycle (3) has been prepared as shown in Scheme 1 [R. Faure, E.—J. Vincent, R. M. Claramunt, J. M. Fabrega, and J. Elguero, *Tetrahedron*, 32, 341 (1976)]. Reaction of 3-amino-1,2,4-triazole (1) with bromoacetaldehyde dimethyl acetal in the presence of sodium ethoxide gives a mixture of alkylated products from which 2 is isolated in modest yield. Treatment of 2 with concentrated sulfuric acid results in cyclization to 3. [NOTE: More than one numbering system for imidazo[1,2-b][1,2,4]triazoles has been used in the literature. The Chemical Abstracts numbering system shown for 3 will be used here throughout.]

SCHEME 1

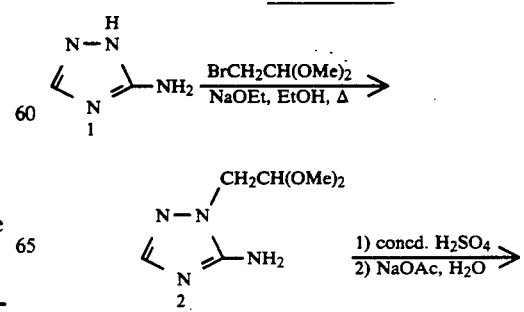

-continued
SCHEME 1

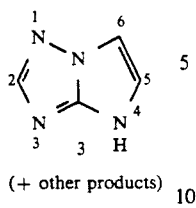

(+ other products)

Substituted imidazo[1,2-b]triazoles have also been prepared by a different route in which the imidazole ring is constructed first, as shown in Scheme 2 [A. Hetzheim and G. Manthey, *Chem. Ber.*, 103, 2845 (1970); A. Hetzheim, H. Pusch, and H. Beyer, *Chem. Ber.*, 103, 3533 (1970); J. A. Bogie and T. Norris, *Res. Discl.*, 162, 73 (1977)]. A 2-amino-1,3,4-oxadiazole 4 is alkylated with the α-bromoketone 5 to give the salt 6, which upon heating with ammonia is converted to the 1-acylamino-2-aminoimidazole derivative 7. Heating 7 with a mixture of phosphorus oxychloride and polyphosphoric acid results in cyclization to the imidazo[1,2-b][1,2,4]triazole 8. However, this method has not been successful for the synthesis of 3-substituted-3H-imidazo[1,2-b][1,2,4]triazoles. A 2-(substituted amino)-imidazole derivative 9 prepared from 6 reportedly fails to cyclize [A. Hetzheim, H. Pusch, and H. Beyer, *Chem. Ber.* 103, 3533 (1970)].

SCHEME 2

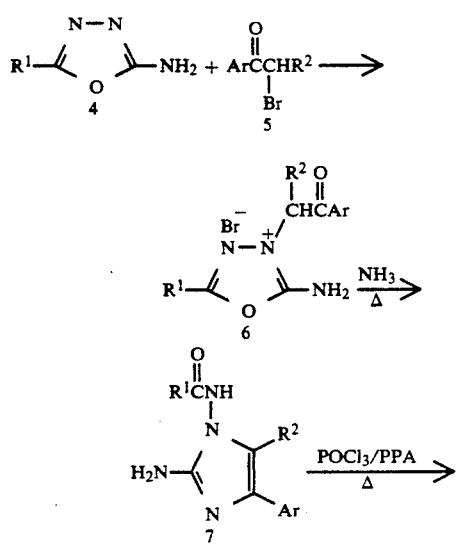

-continued
SCHEME 2

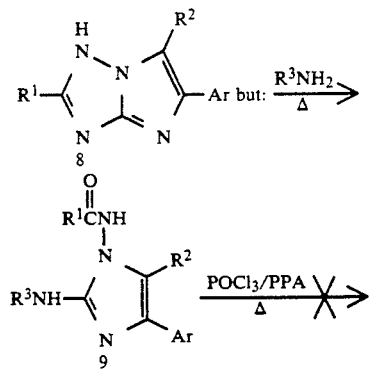

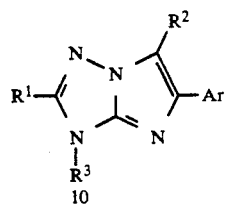

2-Amino-5,6-disubstituted imidazo[1,2-b]-[1,2,4]triazoles 13 (Scheme 3) have been synthesized from 3,5-diamino-1,2,4-triazole (11) by acid-catalyzed condensation with acyloins 12 of (for R=phenyl) by heating with desyl chloride (14) [A. Kreutzberger and B. Meyer, *Chem. Ber.*, 105, 1810 (1972)].

SCHEME 3

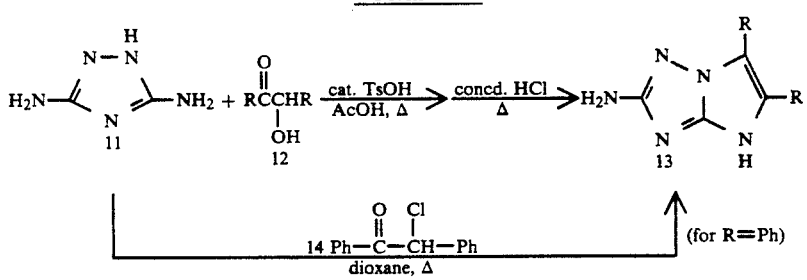

In a similar reaction (Scheme 4), a 2-methylthio-3,5,6-triaryl-3H-imidazo[1,2-b][1,2,4]triazole 16 has been obtained by heating the aminotriazole 15 with desyl chloride (14) [H. Beyer, E. Bulka, and K. Dittrich, *J. Prakt. Chem.*, 302, 280 (1965)]. An analogous reaction of 3-amino-5-methylthio-1,2,4-triazole with phenacyl bromide reportedly failed [A. Sitte, R. Wessel, and H. Paul, *Monatsh. Chem.*, 106, 1291 (1975)], although the intermediate phenacyltriazole could be prepared by an alternative route and cyclized to the imidazo-[1,2-b][1,2,4]triazole upon heating at reflux with 40% hydrobromic acid (A. Sitte, et al., op. cit.).

SCHEME 4

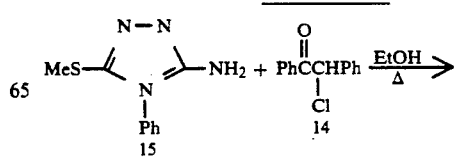

-continued
SCHEME 4

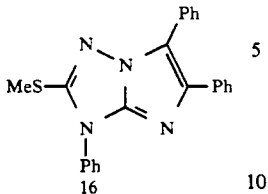

An alternative route to 2-alkylthio-3-substituted-3H-imidazo[1,2-b][1,2,4]triazoles related to 16 is shown in Scheme 5. A 1-amino-2-(substituted amino)-imidazole of structure 17 reacts with carbon disulfide to give the bicyclic thione 18 [A. Hetzheim, H. Pusch, and H. Beyer, Chem. Ber. 103, 3533 (1970)]. Alkylation of 18 with an alkyl bromide in the prescence of a base such as triethylamine or N,N-diisopropylethylamine generates 19.

SCHEME 5

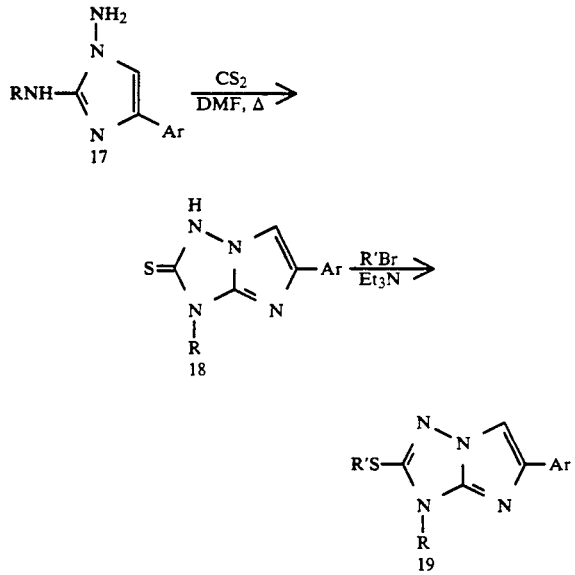

Still another pathway to compounds of similar structure is illustrated in Scheme 6 [P. Molina, A. Lorenzo, and E. Aller, *Synthesis*, 843 (1989)] Treatment of the 1-amino-2-methylthioimidazole 20 with an isothiocyanate 21 yields the thiourea 22. Treatment of 22 with methyl iodide gives the S-methyl derivative (usually not isolated), which upon heating cyclizes to give the imidazo[1,2-b][1,2,4]triazole 24 (equivalent to 19, $R^1$=CH$_3$). A related synthesis of 2-(arylamino)-3,5-diarylimidazo[1,2-b][1,2,4]triazoles has been reported [P. Molina, et al., *Heterocycles*, 27, 161 (1988)].

SCHEME 6

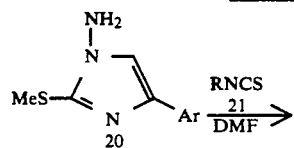

-continued
SCHEME 6

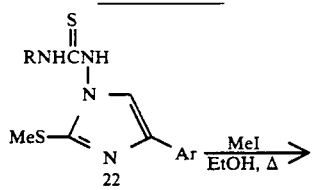

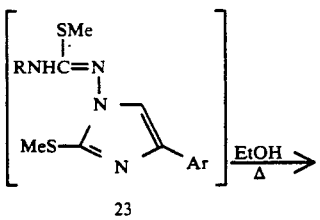

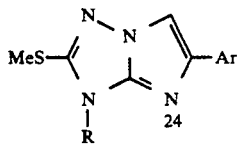

Related to Scheme 6 is a synthetic method which has been used to prepare 2,3,5-triarylimidazo[1,2-b][1,2,4]triazoles 29 (Scheme 7) [P. Molina, M. A. Lorenzo, and E. Aller, *J. Chem. Res.* (S), 262 (1989); P. Molina, A. Lorenzo, M. J. Vilaplana, E. Aller, and J. Planes, *Heterocycles*, 27, 1935 (1988)]. The 1-aminotriazole 20 is converted to the iminophosphorane 25 upon reaction with triphenyl-phosphine dibromide. Treatment of 25 with the acid chloride 26 gives the imidoyl chloride 27. Heating 27 with the amine 28 affords the imidazotriazole 29.

A route to 2-alkyl-5-aryl-3-methylimidazo[1,2-b][1,2,4]triazoles 33 from the aminotriazoles 30 is shown in Scheme 8 [F. S. Babichev, L. al' Yusofi, V. N. Bubnovskaya, and E. V. Boyko, *Ukr. Khim. Zh.* (Russ. Ed.), 50, 1279 (1984)]. Treatment of 30 with the phenacyl bromide 31 gives the salt 32, which cyclizes upon heating with anhydrous perchloric acid (or concentrated sulfuric acid) in acetic acid to give, after neutralization, the imidazotriazole 33. Subsequent nitrosation or nitration at the 6-position can be carried out to give 34a,b [F. S. Babichev, L. al' Yusofi, and V. N. Bubnovskaya, *Ukr. Khim. Zh.* (Russ. Ed.), 51, 431 (1985)]. Nitration or bromination at the 6-position of 5-arylimidazo[1,2-b][1,2,4]triazoles has been reported earlier by Hetzheim [A. Hetzheim, H. Pusch, and H. Beyer, *Chem. Ber.* 103, 3533 (1970)].

SCHEME 7

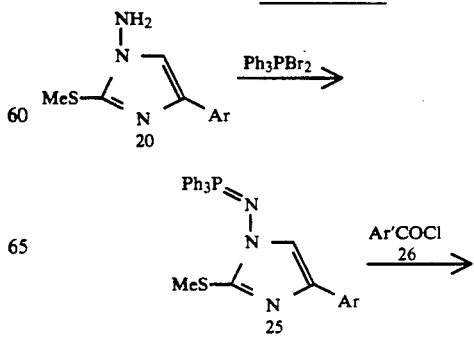

SCHEME 7 -continued

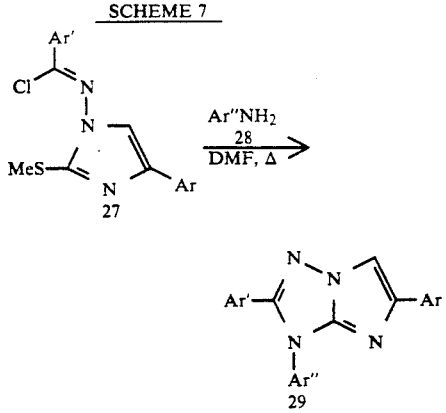

bec, R. Milcent, and G. Barbier [*J. Heterocycl. Chem.*, 21, 1689 (1984)] to yield the ester thiosemicarbazone 36. Treatment of 36 with methyl iodide followed by neutralization affords the S-methylisothiosemicarbazone 37. Upon treatment of 37 with the amine 38 (EP 0412594 published 2-13-91, Merck Case No. 17959IA) at or just above room temperature, the adduct 39 may be isolated. In the presence of m-chloroperoxybenzoic acid (MCPBA), 39 readily cyclizes to the aminotriazole 40. When 40 is heated with an appropriate α-halocarbonyl compound 41, the intermediate salt 42 is obtained. Cyclization of 42 is preferably accomplished by heating in polyphosphoric acid (PPA) at about 80° C.

SCHEME 8

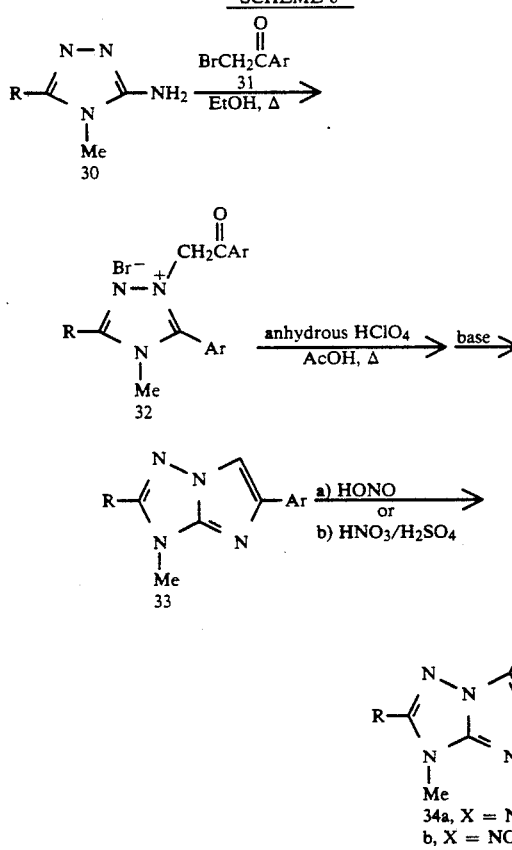

SCHEME 9

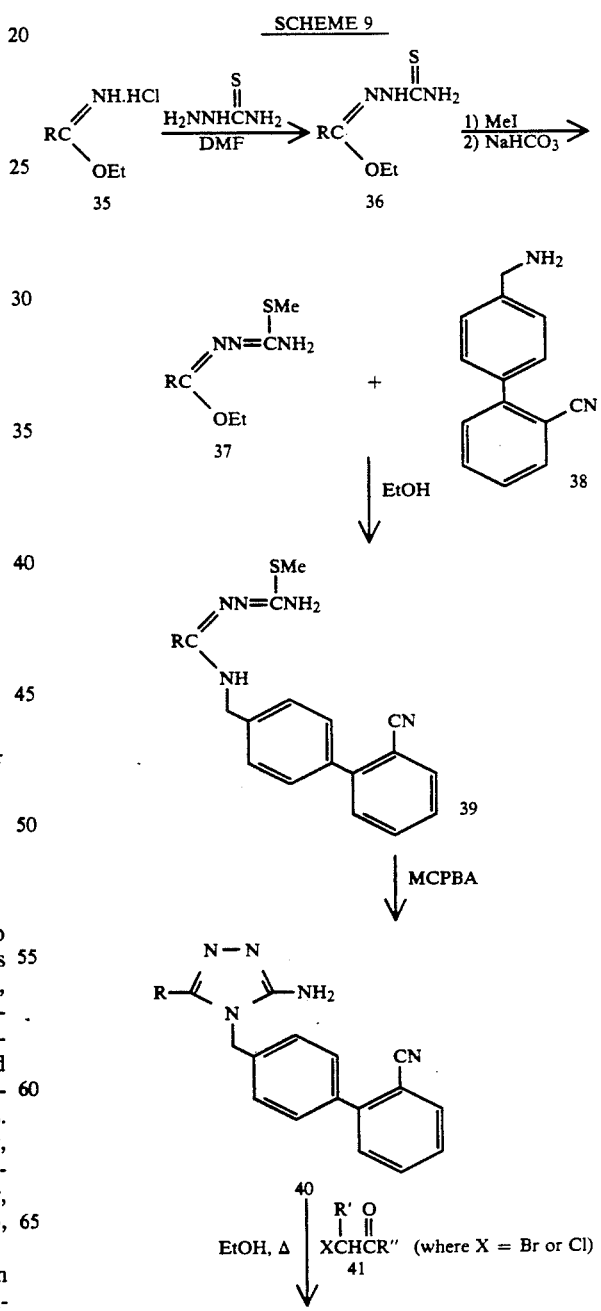

Many of the foregoing schemes can be adapted to prepare compounds of Formula I. An illustration of this is shown in Scheme 9. This scheme includes a new, regiospecific synthesis of 3-amino-4,5-disubstituted-4H-1,2,4-triazoles. In the past, such compounds have generally been made by ring closure reactions of substituted aminoguanidines with carboxylic acids or their derivatives, often leading to isomeric mixtures of products. [See, for example, C. Temple and J. A. Montgomery, "Triazoles: 1,2,4" (Vol. 37 of "The Chemistry of Heterocyclic Compounds", A. Weissberger and E. C. Taylor, eds), Wiley-Interscience, New York, 1981, pp. 152-153, and references therein.]

First, the imidate hydrochloride 35 is reacted with thiosemicarbazide according to the method of F. Mal- -continued
SCHEME 9

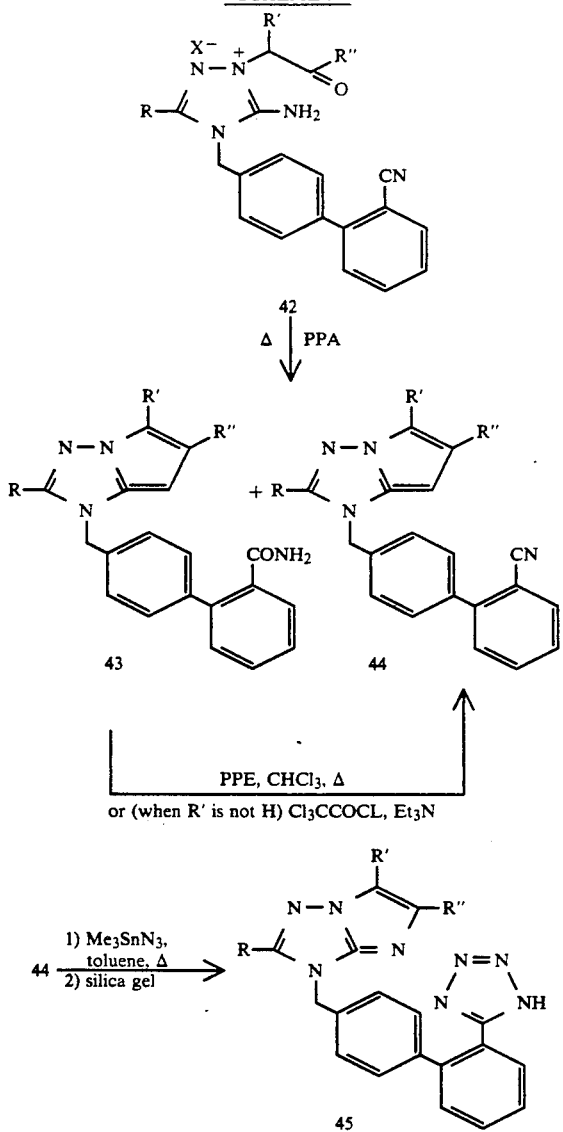

Typically obtained is a mixture of imidazo[1,2-b]-[1,2,4]triazoles 43 and 44, bearing carboxamide and cyano substituents, respectively, on the biphenyl side chain. The carboxamide is generally the major product. The amide 43 may be dehydrated to the nitrile 44 by heating with polyphosphate ester (PPE). An attractive alternative method for the dehydration of 43 to 44, in cases where R' is not hydrogen, is the use of trichloroacetyl chloride in the presence of triethylamine. Depending on the nature of R' and R", the reaction of 40 with 41 may in some circumstances lead directly to the imidazotriazole 44. An example of this is the reaction of 40 (R=butyl) with α-bromophenylacetaldehyde (41, R'=Ph, R"=H). Finally, the cyano group of 44 is converted to the tetrazole 45 by heating with trimethyltin azide in a suitable solvent such as toluene or xylene according to methods described in EP 291,969, followed by destannylation in the presence of silica gel.

Schemes 10 and 11 show examples of the synthesis of analogs of 45 in which the tetrazole group ($R^1$ in Formula I) is replaced by other acidic functional groups. Thus, in Scheme 10 the amine 46 (EP 0409332 published 1-23-91, Merck Case No. 17960IA) which bears a t-butyl ester substituent is converted by the methods of Scheme 9 to the imidazo[1,2-b] [1,2,4]triazole 47. Deprotection of the t-butyl ester with trifluoroacetic acid (TFA) yields the free carboxylic acid 48. This may be further converted to the acylsulfonamide 50. For example, 48 may be reacted with 1,1'-carbonyldiimidazole (CDI) to give an N-acylimidazole intermediate. This is treated with a sulfonamide 49 in the prescence of 1,8-diazabicyclo-[5.4.0]undec-7-ene (DBU) to give 50.

SCHEME 10

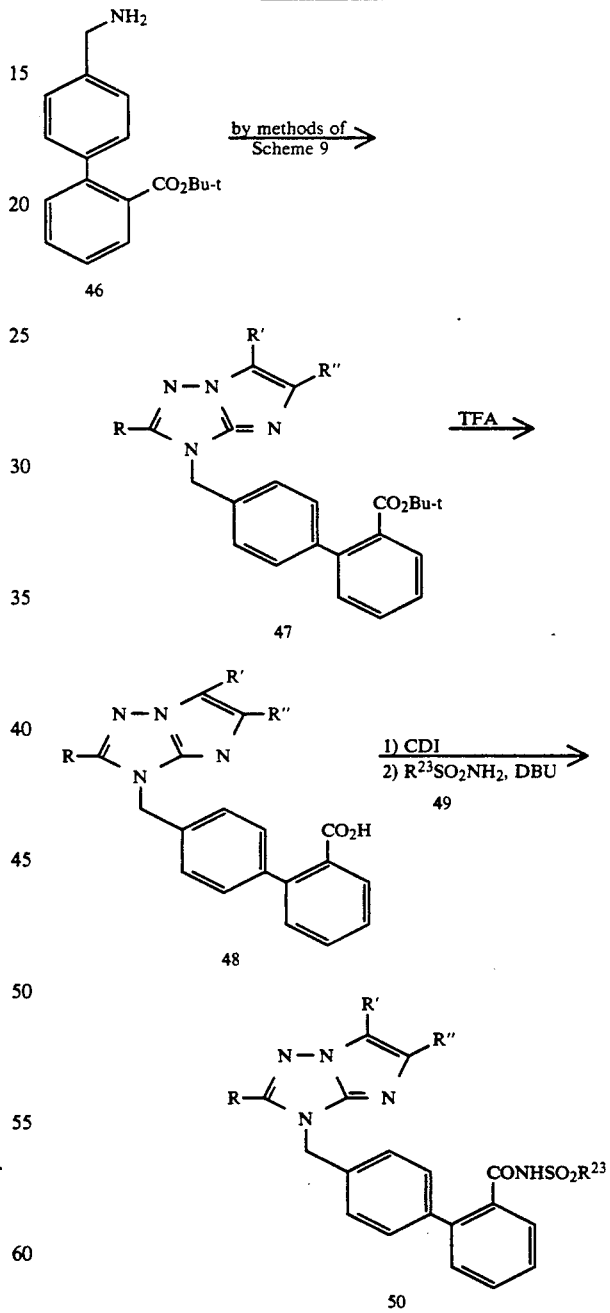

The synthesis of analogs of 50 with a reversed acylsulfonamide grouping is outlined in Scheme 11. Reaction of 2-bromobenzenesulfonyl chloride (51) with an excess of t-butylamine yields the t-butylsulfonamide 52. The trimethylstannyl derivative 54 is prepared from p-tolylmagnesium bromide (53) by treatment with trimethyltin chloride at −35° C. to room temperature. Cross-coupling of 54 with 52 catalyzed by bis(triphenylphosphine)palladium (II) chloride in DMF at about 90° C. affords the biphenyl derivative 55 with N-bromosuccinimide (NBS) in carbon tetrachloride in the presence of an initiator such as 2,2'-azobis(isobutyronitrile) (AIBN). The bromo compound 56 is treated with lithium azide in DMSO to give an intermediate azido derivative, which is reduced with triphenylphosphine to the amine 57. By the methods of Scheme 9, 57 is transformed to the imidazo[1,2-b][1,2,4]triazole 58, which is deprotected with trifluoroacetic acid to give the free sulfonamide 59. This can be treated, in a manner analogous to Scheme 10, with the N-acylimidazole derivative of the carboxylic acid 60 to provide the acylsulfonamide 61.

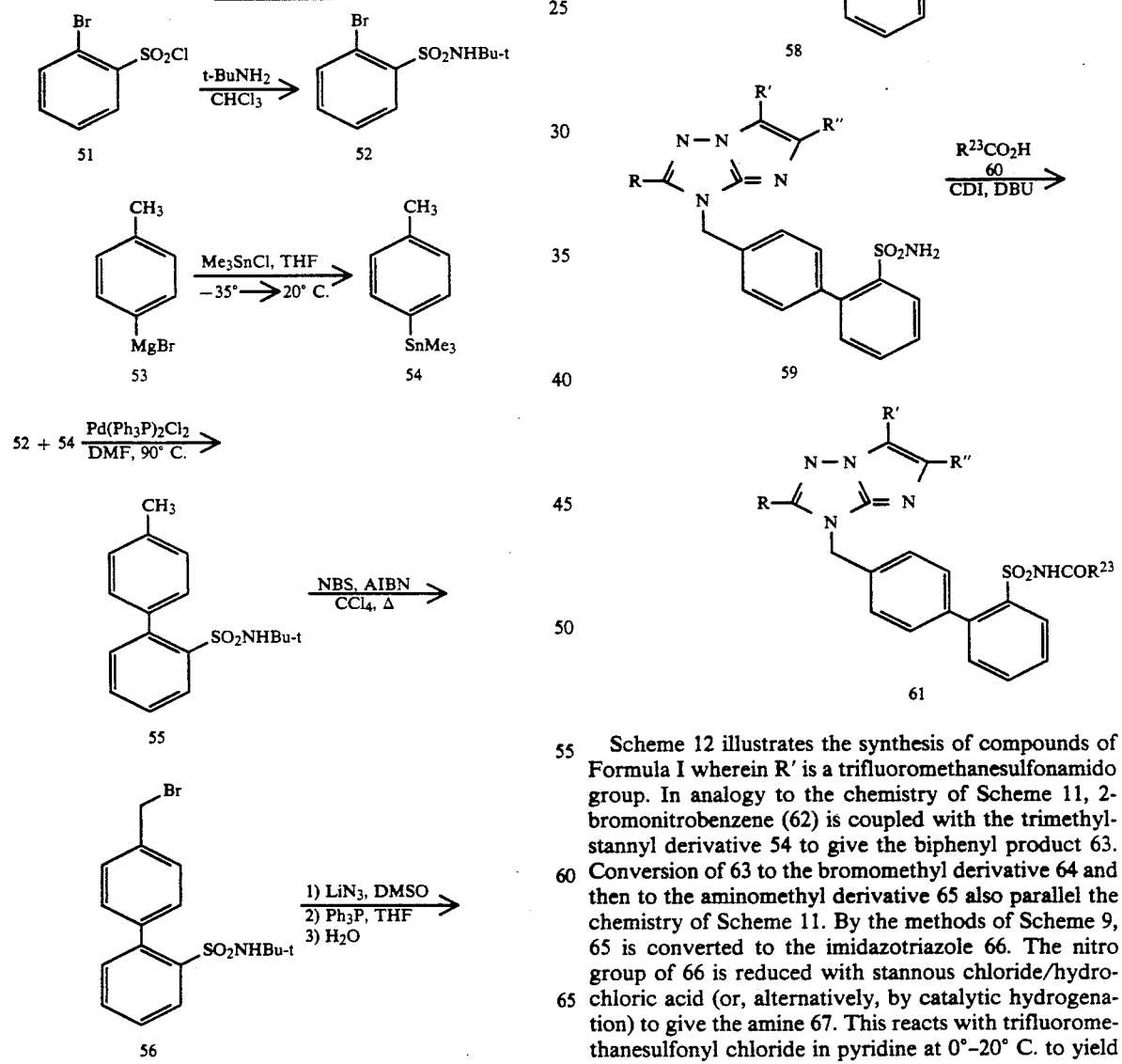

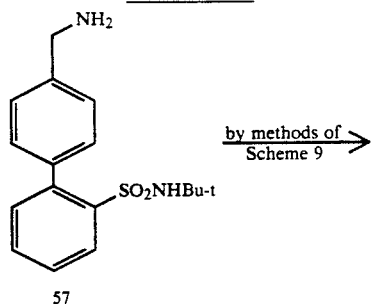

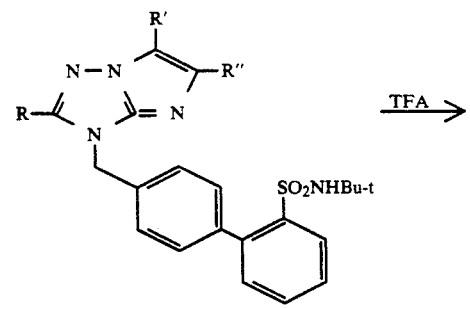

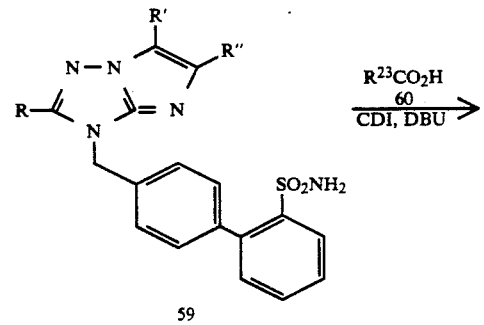

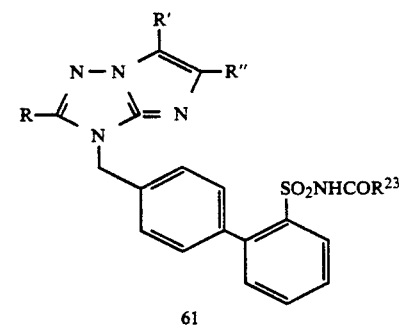

Scheme 12 illustrates the synthesis of compounds of Formula I wherein R' is a trifluoromethanesulfonamido group. In analogy to the chemistry of Scheme 11, 2-bromonitrobenzene (62) is coupled with the trimethylstannyl derivative 54 to give the biphenyl product 63. Conversion of 63 to the bromomethyl derivative 64 and then to the aminomethyl derivative 65 also parallel the chemistry of Scheme 11. By the methods of Scheme 9, 65 is converted to the imidazotriazole 66. The nitro group of 66 is reduced with stannous chloride/hydrochloric acid (or, alternatively, by catalytic hydrogenation) to give the amine 67. This reacts with trifluoromethanesulfonyl chloride in pyridine at 0°–20° C. to yield the trifluoromethanesulfonamide 68.

SCHEME 12

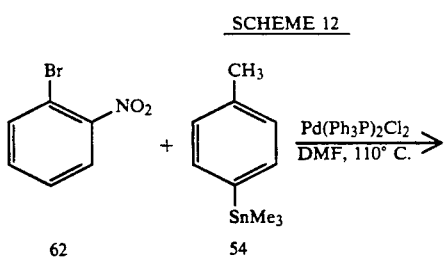

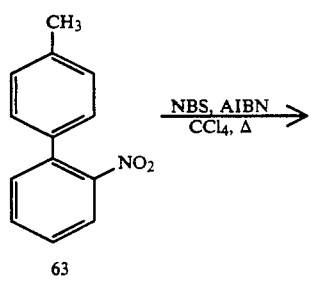

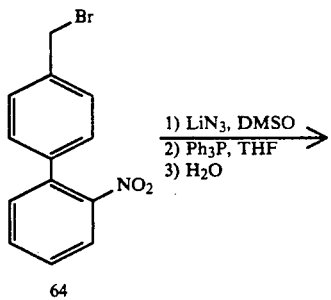

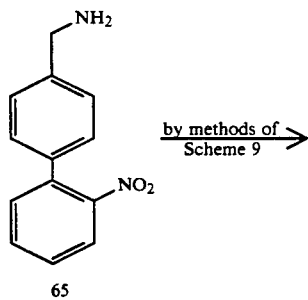

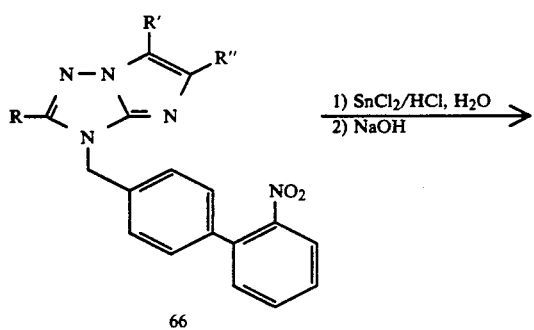

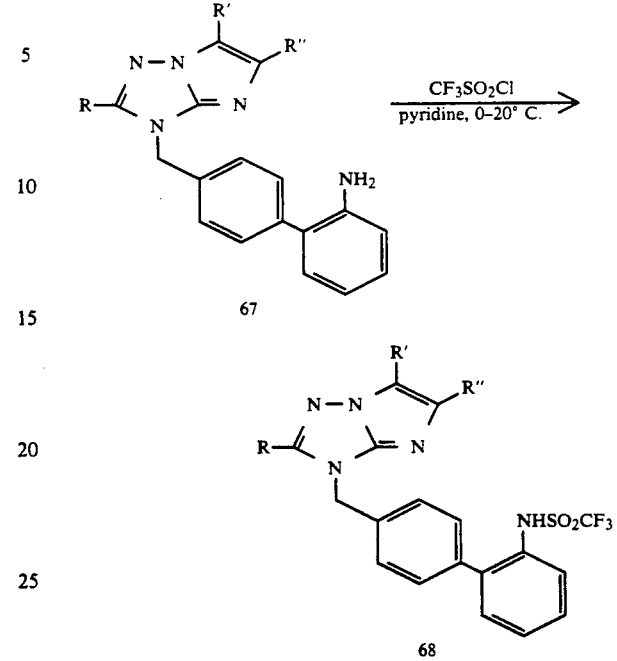

In compounds of Formula I, the $R^7$ and $R^8$ substituents may undergo a variety of further transformations, and new $R^7$ and $R^8$ substituents may also be introduced by replacement of hydrogen by other groups such as bromo, nitro, or acyl in an electrophilic substitution reaction.

Although the reaction schemes described herein are reasonably general, it will be understood by those skilled in the art of organic synthesis that one or more functional groups present in a given compound of formula I may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 mL) homogenized, and then centrifuged. The mixture was filtered through a cheesecloth and the supernatant was centrifuged for 30 minutes at 20,000 rpm at 4° C. The pellet thus obtained was resuspended in 30 mL of 50 mM Tris-5 mM $MgCl_2$ buffer containing 0.2% Bovine Serum Albumin and 0.2 mg/mL Bacitracin and the suspension was used for 100 assay tubes. Samples tested for screening were done in duplicate. To the membrane preparation (0.25 mL) there was added $^{125}I$-$Sar^1Ile^8$-angiotensin II [obtained from New England Nuclear] (10 mL; 20,000 cpm) with or without the test sample and the mixture was incubated at 37° C. for 90 minutes. The mixture was then diluted with ice-cold 50 mM Tris-0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration ($IC_{50}$) of potential AII antagonist which gives 50% displacement of the total specifically bound $^{125}I$-$Sar^1Ile^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethanesulfonyl fluoride (PMSF) (0.1 mM)]. (For screening of compounds, generally duplicates of tubes are used). To the membrane preparation (0.5 mL) there was added $^3H$-angiotensin II (50 mM) (10 mL) with or without the test sample and the mixture was incubated at 37° C. for 1 hour. The mixture was then diluted with Tris buffer (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration ($IC_{50}$) of potential AII antagonist which gives 50% displacement of the total specifically bound $^3H$-angiotensin II was presented as a measure of the efficacy of such compounds as AII antagonists.

Using the methodology described above, representative compounds of the invention were evaluated and found to exhibit an activity of at least $IC_{50} < 50$ mM thereby demonstrating and confirming the utility of the compounds of the invention as effective AII antagonists.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectibles, as well as topical ocular formulations in the form of solutions, ointments, inserts, gels and the like.

Pharmaceutical formulations prepared to treat intraocular pressure would typically contain about 0.1% to 15% by weight, and preferably 0.5% to 2.0% by weight of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Preferably, the dosage range will be about 2.5 to 250 mg per patient per day; more preferably about 2.5 to 75 mg per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidine sulfate, hydralazine hydrochloride, hydrochlorothiazide, metolazone, metoprolol tartate, methyclothiazine, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetozolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflunisal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg), chlorothiazide (125-2000 mg), ethacrynic acid (15-200 mg), amiloride (5-20 mg), furosemide (5-80 mg), propranolol (20-480 mg), timolol maleate (5-60 mg), methyldopa (65-2000 mg), felodipine (5-60 mg), nifedipine (5-60 mg), and nitrendipine (5-60 mg). In addition, triple drug combinations of hydrochlorothiazide (15-200 mg) plus miloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of. wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers such as nimodipine, and nootropic agents such as piracetam.

In order to achieve optimal anxiolytic activity, the compounds of this invention may be combined with other anxiolytic agents such as alprazolam, lorazepam, diazepam, and buspirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered nor construed as limiting the invention set forth in the claims appended hereto.

EXAMPLE 1

2-butyl-6-methyl-5-phenyl-3-[[2'-(5-tetrazolyl)biphenyl-4-yl]methyl]-3H-imidazo[1,2-b][1,2,4]triazole

Step A: Ethyl Valerate Thiosemicarbazone

A solution of 10.79 g (65 mmol) of ethyl valerimidate hydrochloride [prepared by method of A. J. Hill and I. Rabinowitz, *J. Am. Chem. Soc.*, 48, 734 (1926)] in 130 ml of dry DMF was stirred at room temperature as 5.91 g (65 mmol) of thiosemicarbazide was added. Stirring was continuted under $N_2$. After 2.5 hours, by which time TLC (19:1 $CH_2Cl_2$-MeOH) indicated complete conversion of thiosemicarbazide to a higher $R_f$ product, the mixture was partitioned between 1 L of $H_2O$, then dried over $MgSO_4$, filtered, and concentrated in vacuo. The residual oil, upon drying in vacuo (<1 mm) overnight, solidified to yield 11.05 g (84%) of nearly white solid, mp 73°-74.5° C.; homogeneous by TLC in 97:3 $CH_2Cl_2$-MeOH. NMR indicated a mixture of syn and anti isomers.

Mass spectrum (FAB): m/e 204 (M+1).

Analysis ($C_8H_{17}N_3OS$): Calculated: C, 47.26; H, 8.43; N, 20.67 and Found: C, 46.92; H, 8.21; N, 20.40.

$^1$H NMR (CDCl$_3$, 300 MHz, ppm): δ0.91 (t, 3H), 1.25-1.4 (m, 5H), 1.55 (m, 2H), 2.31 (t, 2H), 4.0-4.15 (m, 2H), 6.03 (br s, 1H), 6.80, 6.95 (minor and major br s, 2H total), 8.05, 8.97 (minor and major br s, 1H total).

Step B: Ethyl Valerate S-Methylisothiosemicarbazone

To a stirred solution of 11.02 g (54.2 mmol) of ethyl valerate thiosemicarbazone (from Step A) in 50 ml of $CH_2Cl_2$ was added 6.75 ml (15.39 g, 108.4 mmol) of methyl iodide. Stirring was continued under $N_2$, and a mild exotherm was observed. After 2.5 hours, by which time TLC (19:1 $CH_2Cl_2$-MeOH) indicated complete reaction, the solution was treated gradually with ether (150-175 ml total) while being agitated, until the point where crystallization began. The mixture was allowed to stand for more than 1 hour before the solid was collected on a filter, washed with ether, and dried under $N_2$. The solid was partitioned between 100 ml of saturated aqueous sodium bicarbonate and a mixture of 200 ml of ether and 50 ml of $CH_2Cl_2$. The organic phase was dried over $Na_2SO_4$, filtered, and concentrated in vacuo at ≦30° C. The residue was vacuum-dried (<1 mm) at room temperature to yield 4.85 g (41%) of white solid, mp 80°-82° C.; satisfactory purity by TLC in 19:1 $CH_2Cl_2$-MeOH.

Mass spectrum (FAB): m/e 218 (M+1).

Analysis ($C_9H_{19}N_3OS$): Calculated: C, 49.74; H, 8.81; N, 19.33 and Found: C, 49.42; H, 8.59; N, 19.06.

$^1$H NMR (CDCl$_3$, 300 MHz, ppm): δ0.90 (t, 3H), 1.29 (t, 3H), 1.36 (m, 2H), 1.58 (m, 2H), 2.27 (t, 2H), 2.40 (s, 3H), 4.31 (br q, 2H), 5.07 (br s, 2H).

Step C: N-[(2'-Cyanobiphenyl-4-yl)methyl]valeramide S-Methylisothiosemicarbazone A mixture of 5.50 g (25.3 mmol) of ethyl valerate S-methylisothiosemicarbazone (from Step B), 6.55 g (31.5 mmol) of [(2'-cyanobiphenyl-4-yl)methyl]amine (EP 0412594 published Feb. 13, 1991, Merck Case No. 17959IA), and 57 ml of dry EtOH was stirred under $N_2$ at room temperature for 6 days and then concentrated in vacuo at ≦30° C. The residue was chromatographed on a column of silica gel (38×8.8 cm) packed in $CH_2Cl_2$. Gradient elution with 0.5-2% MeOH in $CH_2Cl_2$ and concentration of combined product fractions gave 6.86 g (71%) of the title compound as a yellow gum; satisfactory purity by TLC in 19:1 $CH_2Cl_2$-MeOH. NMR indicated a mixture of syn and anti isomers.

Mass spectrum (FAB): m/e 380 (M+1).

$^1$H NMR (CDCl$_3$, 300 MHz, ppm): δ0.91 (m, 3H), 1.37 (m, 2H), 1.55-1.75 (m, 2H), 2.28, 2.73 (t, 2H total), 2.40 2.58 (s, 3H total), 4.45 (d, 2H), 4.82, 5.18 (minor and major br s, 2H total), 6.51 (br t, 1H), 7.35-7.55 (m, 6H), 7.63 (dd, 1H), 7.75 (d, 1H).

Upon further elution of the column with 95:5:0.5 $CH_2Cl_2$-MeOH-concd. NH$_4$OH, 1.59 g of unreacted [(2'-cyanobiphenyl-4-yl)methyl]amine was recovered.

Step D: 3-Amino-5-butyl-4-[2'-cyanobiphenyl-4-yl)methyl]-4H-1,2,4-triazole

A solution of 6.86 g (18.1 mmol) of N-[(2'-cyanobiphenyl-4-yl)methyl]-valeramide S-methylisothiosemicarbazone (from Step C) in 55 ml of $CH_2Cl_2$ was stirred at room temperature as 6.09 g (28.2 mmol, based on 80% purity) of m-chloroperoxybenzoic acid was added gradually in small over portions over approximately 1.5 hours. A mild exotherm and some gas evolution was observed during the addition. After 5 hours at room temperature, the reaction mixture was added to 50 ml of 10% NaOH (aqueous) and 150 ml of ether. The resulting mixture was agitated, and precipitation of product occurred. The precipitate was collected on a filter and washed thoroughly with $H_2O$, then with some ether. This material was dried in vacuo (<1 mm) at 100° C. overnight to give 3.56 g of cream-colored solid, mp 206°-207° C.; essentially homogeneous by TLC in 90:10:0.1 $CH_2Cl_2$-MeOH-AcOH. After partial evaporation of the ether phase of the filtrate, additional precipitate separated. This was isolated as described above to afford 0.28 g of satisfactory second crop. The total yield was 3.84 g (64%).

Mass spectrum (FAB): m/e 332 (M+1).

Analysis ($C_{20}H_{21}N_5$): Calculated: C, 72.48; H, 6.39; N, 21.13 Found: C, 72.40; H, 6.56; N, 21.03.

$^1$H NMR (CDCl$_3$, 300 MHz, ppm): δ0.90 (t, 3H), 1.38 (m, 2H), 1.72 (m, 2H), 2.63 (t, 2H), 4.06 (br s, 2H), 4.99 (s, 2H), 7.20 (d, 2H), 7.4-7.5 (m, 2H), 7.55 (d, 2H), 7.65 (dd, 1H), 7.75 (d, 1H).

Step E: 5-Amino-1-(1-benzoylethyl)-3-butyl-4-[(2'-cyanobiphenyl-4-yl)methyl]-4H-1,2,4-triazolium bromide A mixture of 211 mg (0.636 mmol) of 3-amino-5-butyl-4-[(2'-cyanobiphenyl-4-yl)methyl]-4H-1,2,4-triazole (from Step D), 101 μl (141 mg, 0.664 mmol) of 2-bromopropiophenne, and 4.5 ml of absolute EtOH was stirred under $N_2$ in an oil bath at 80° C. for 8 hours. The solution was then cooled and concentrated in vacuo. Vacuum-drying (<1 mm) at room temperature for several hours afforded 315 mg (91%) of the title compound as a stiff, yellow foam, suitable for use without further purification.

Mass spectrum (FAB): m/e 484 (M+ for cation).

$^1$H NMR (DMSO-d$_6$, 400 MHz, ppm): δ0.69 (t, 3H), 1.10 (m, 2H), 1.36 (m, 2H), 1.72 (d, 3H), 2.58 (t, 2H), 5.38 (s, 2H), 6.28 (q, 1H), 7.22 (d, 2H), 7.55-8.0 (m, 11H).

$^1$H NMR (CDCl$_3$, 400 MHz, ppm): δ0.83 (t, 3H), 1.24 (m, 2H), 1.56 (m, 2H), 1.79 (d, 3H), 2.49 (t, 2H), 5.38 (d, 1H), 5.86 (d, 1H), 7.06 (q, 1H), 7.23 (d, 2H), 7.35-7.55

(m, 7H), 7.62 (dd, 1H), 7.73 (d, 1H), 8.05 (d, 2H), 8.92 (br s, 2H).

Step F:
2-Butyl-3-[(2'-cyanobiphenyl-4-yl)methyl]-6-methyl-5-phenyl-3H-imidazo[1,2-b][1,2,4]triazole A mixture of 303 mg (0.556 mmol) of 5-amino-1-(1-benzoylethyl-3-butyl-4-[(2'-cyanbiphenyl-4-yl)-methyl]-4H-1,2,4-triazolium bromide (from Step E) and 6 g of polyphosphoric acid was stirred at 80° C. under $N_2$ for 5 hours. The cooled mixture was treated with an excess of ice. After the ice had melted, the water was decanted off, and the residue was partitioned between EtOAc and saturated aqueous NaHCO$_3$. The organic phase was dried over Na$_2$SO$_4$, filtered, and concentrated in vacuo. The residual oil was dissolved in a minimum volume of CH$_2$Cl$_2$ and treated with 200 μl (145 mg, 1.43 mmol) of triethylamine. The resulting solution was cooled to 0° C. and stirred under N$_2$ as 137 μl (223 mg, 1.23 mmol) of trichloroacetyl chloride was added. The solution was allowed to warm to room temperature. After 1 hour at room temperature, the solution was concentrated in vacuo. The residue was leached with 25 ml of ether. The filtered ether solution was washed with 25 ml of 0.2N HCl and then with 25 ml of 0.2N NaOH. The ethereal phase was dried (Na$_2$SO$_4$), filtered, and evaporated. Column chromatography of the residue on silica gel (elution with 99:1 and then 98:2 CH$_2$Cl$_2$-MeOH) afforded 95.0 mg (39%) of the title compound as a brown solid of indefinite mp, suitable for use in the next step; homogeneous by TLC in 19:1 CH$_2$Cl$_2$-MeOH.

Mass spectrum (FAB): m/e 446 (M+1).
$^1$H NMR (DMSO-d$_6$, 400 MHz, ppm): δ0.85 (t, 3H), 1.35 (m, 2H), 1.63 (m, 2H), 2.54 (s, 3H), 5.38 (s, 2H), 7.21 (dd, 1H), 7.37 (dd, 2H), 7.48 (d, 2H), 7.55–7.6 (m, 4H), 7.67 (d, 2H), 7.76 (dd, 1H), 7.93 (d, 1H).

Step G:
2-Butyl-6-methyl-5-phenyl-3-[[2'-(5-tetrazolyl)biphenyl-4-yl]methyl]-3H-imidazo[1,2-b][1,2,4]triazole A mixture of 95.0 mg (0.213 mmol) of 2-butyl-3-[(2'-cyanobiphenyl-4-yl)methyl]-6-methyl-5-phenyl-3H-imidazo[1,2-b][1,2,4]triazole (from Step F), 158 mg (0.769 mmol) of trimethyltin azide, and 2.0 ml of toluene was stirred at reflux under N$_2$ for 24 hours. The mixture was concentrated in vacuo, and the residue was treated with 3 ml of dry MeOH and 1.0 g of silica gel. The resulting mixture was stirred at room temperature in a stoppered flask overnight. The solvent was removed by rotary evaporation in vacuo to give a dry powder, which was added as a slurry in CH$_2$Cl$_2$ to the top of a column of silica gel (26×2.5 cm) packed in CH$_2$Cl$_2$. Gradient elution of the column with 1.5% MeOH in CH$_2$Cl$_2$ and concentration of the product fractions yielded 40.4 mg (37%) of the title compound as a yellow gum, which, upon trituration with ether, was transformed to a tan solid (28 mg, 25%), mp 207°–208° C.; homogeneous by TLC in 90:10:0.1 CH$_2$Cl$_2$-MeOH-AcOH.

Mass spectrum (FAB): m/e 489 (M+1).
Analysis [C$_{29}$H$_{28}$N$_5$.0.5H$_2$O.0.25 C$_4$H$_{10}$O (ether)]: Calculated: C, 69.81; H, 6.15; N, 21.71 and Found: C, 70.08; H, 6.03; N, 21.67.
$^1$H NMR (DMSO-d$_6$, 400 MHz, ppm): δ0.86 (t, 3H), 1.34 (m, 2H), 1.60 (m, 2H), 2.53 (s, 3H), 2.77 (t, 2H), 5.27 (s, 2H), 7.09 (d, 2H), 7.21 (dd, 1H), 7.27 (d, 2H), 7.38 (dd, 2H), 7.45–7.7 (m, 6H).

EXAMPLE 2

2-Butyl-5-phenyl-3-[[2'-(5-tetrazolyl)biphenyl-4-yl]methyl]3H-imidazo[1,2-b][1,2,4]triazole Step A:
5-Amino-3-butyl-4-[(2'-cyanobiphenyl-4-yl)methyl]-1-phenacyl-4H-1,2,4-triazolium bromide Reaction of 3-amino-5-butyl-4-[(2'-cyanobiphenyl-4-yl)methyl]-4H-1,2,4-triazole (from Example 1, Step D) with phenacyl bromide (2-bromoacetophenone) according to the procedure of Example 1, Step E, gave an 86% yield of the title compound as a stiff, yellow foam, suitable for use without further purification.

Mass spectrum (FAB): m/e 450 (M+ for cation).
$^1$H NMR (CDCl$_3$, 400 MHz, ppm): δ0.81 (t, 3H), 1.31 (m, 2H), 1.59 (m, 2H), 2.51 (t, 2H), 5.63 (s, 2H), 5.63 (s, 2H), 6.12 (s, 2H), 7.36 (d, 2H), 7.4–7.65 (m, 8H), 7.72 (d, 1H), 7.96 (d, 2H), 8.82 (s, 2H).

Step B:
2-Butyl-3-[(2'-carbamoylbiphenyl-4-yl)methyl]-5-phenyl-3H-imidazo[1,2-b][1,2,4]triazole and
2-Butyl-3-[(2'-cyanobiphenyl-4-yl)methyl]-5-phenyl-3H-imidazo[1,2-b][1,2,4]triazole The entire quantity of 5-amino-3-butyl-4-[(2'-cyanobiphenyl-4-yl)methyl]-1-phenacyl-4H-1,2,4-triazolium bromide, prepared as in Step A from 0.637 mmol of the aminotriazole precursor, was treated with 5 g of polyphosphoric acid and stirred under N$_2$ at 85° C. for 6 hours. The cooled reaction mixture was then treated with ice and allowed to stand for 2 hours. The entire mixture was added to a separatory funnel containing 75 ml of EtOAc, followed by gradual addition of 100 ml of saturated aqueous NaHCO$_3$ (CAUTION: gas evolution). After shaking and separating the layers, the EtOAc phase was washed with an additional 100 ml of saturated NaHCO$_3$ solution. The organic solution was dried over NaSO$_4$, filtered, and concentrated in vacuo. The residual oil was chromatographed on a column of silica gel (24×2.5 cm) packed in CH$_2$Cl$_2$. Gradient elution with 1.5% MeOH in CH$_2$Cl$_2$ and concentration of the appropriate fractions afforded two products. The first product to be eluted consisted of 36.3 mg (13% overall) of 2-butyl-3-[(2'-cyanobiphenyl-4-yl)methyl]-5-phenyl-3H-imidazo[1,2-b][1,2,4]triazole as a yellow oil, homogeneous by TLC in 19:1 CH$_2$Cl$_2$-MeOH.

Mass spectrum (FAB): m/e 432 (M+1).
$^1$H NMR (CDCl$_3$, 400 MHz, ppm): δ0.89 (t, 3H), 1.39 (m, 2H), 1.70 (m, 2H), 2.67 (t, 2H), 5.31 (s, 2H), 5.31 (s, 2H), 7.2–7.65 (m, 11H), 7.73 (d, 1H), 7.80 (d, 2H).

The second product to be eluted consisted of 211 mg (74% overall) of the corresponding carboxamide, 2-butyl-3-[(2'-carbamoylbiphenyl-4-yl)methyl]-5-phenyl-3H-imidazo[1,2-b][1,2,4]triazole as a yellow solid of indefinite mp, homogeneous by TLC in 19:1 CH$_2$Cl$_2$-MeOH.

Mass spectrum (FAB): m/e 450 (M+1).
$^1$H NMR (CDCl$_3$, 400 MHz, ppm): δ0.91 (t, 3H), 1.40 (m, 2H), 1.72 (m, 2H), 2.69 (t, 2H), 5.24 (partially obscured br s, 1H), 5.28 (s, 2H), 5.40 (br s, 1H), 7.2–7.5 (m, 10H), 7.71 (d, 1H), 7.78 (d, 2H).

Step C:
2-Butyl-3-[(2'-cyanobiphenyl-4-yl)methyl]-5-phenyl-3H-imidazo[1,2-b][1,2,4]triazole To 211 mg (0.468 mmol) of 2-butyl-3-[(2'-carbamoyl-biphenyl-4-yl)methyl]-5-phenyl-3H-imidazo-[1,2-b][1,2,4]triazole (from Step B) was added 6 ml of polyphosphate ester (PPE) [M. Cava, M. Lakshmikantham, and M. Mitchell, *J. Org. Chem.*, 34, 2665 (1969)] solution, consisting of approximately a 2:1 ratio of PPE and CDCl₃ (used as a surrogate for alcohol-free chloroform). The mixture was stirred at reflux under N₂ for 3 hours. The solvent was removed by concentration in vacuo. The residue was cooled in an ice bath and treated with an excess of saturated aqueous Na₂CO₃. The mixture was stirred for 1 hour and then shaken with 30 ml of EtOAc. The EtOAc layer was washed with 30 ml of H₂O. The combined aqueous fractions were extracted with an additional portion of EtOAc. The combined organic fractions were dried over NaSO4, filtered, and concentrated. Column chromatography of the residue on silica gel (elution with 1% and then 2% MeOH in CH₂Cl₂) gave 188 mg of a yellow oil, which solidified upon standing; mp 88°-90° C., homogeneous by TLC in 19:1 CH₂Cl₂-MeOH. ¹H NMR indicated the presence of a phosphate ester contaminant, which had co-chromatographed, but the material was suitable for use in the next step.

Mass spectrum (FAB): m/e 432 (M+1).

¹H NMR (CDCl₃, 400 MHz, ppm): δ0.89 (t, 3H), 1.39 (m, 2H), 1.70 (m, 2H), 2.67 (t, 2H), 5.31 (s, 2H), 7.2–7.65 (m, 11H), 7.73 (d, 1H), 7.80 (d, 2H). Phosphate ethyl peaks were observed at 1.35 (t) and 4.23 (m).

Step D:
2-Butyl-5-phenyl-3-[[2'-(5-tetrazolyl)bi-phenyl-4-yl]methyl]-3H-imidazo[1,2-b][1,2,4]-triazole Reaction of 2-butyl-3-[(2'-cyanobiphenyl-4-yl)methyl]-5-phenyl-3H-imidazo[1,2-b][1,2,4]triazole (from Step B and C) with trimethyltin azide according to the procedure of Example 1, Step G, gave a 44% yield of the title compound as a light tan solid, mp >160° C. (gradual); homogeneous by TLC in 90:10:0.1 CH₂Cl₂-MeOH-AcOH.

Mass spectrum (FAB): m/e 475 (M+1).
Analysis [C₂₈H₂₆N₈.0.25 H₂O.0.25 C₄H₁₀O (ether)]: Calculated: C, 70.00; H, 5.84; N, 22.52 and Found: C, 69.83; H, 5.56; N, 22.66.

¹H NMR (CDCl₃, 400 MHz, ppm): δ0.90 (t, 3H), 1.39 (m, 2H), 1.70 (m, 2H), 2.71 (t, 2H), 5.28 (s, 2H), 7.04 (m, 4H), 7.2–7.55 (m, 7H), 7.67 (d, 2H), 7.75 (d, 1H).

EXAMPLE 3

2-Butyl-5-methyl-3-[[2'-(5-tetrazolyl)biphenyl-4-yl]-methyl]-3H-imidazo[1,2-b][1,2,4]triazole

Step A:
1-Acetonyl-5-amino-3-butyl-4-[(2'-cyanobiphenyl-4-yl)methyl]-4H-1,2,4-triazolium chloride Reaction of 3-amino-5-butyl-4-[(2'-cyanobiphenyl-4-yl)methyl]-4H-1,2,4-triazole (from Example 1, Step D) with chloroacetone according to the procedure of Example 1, Step E, gave a 97% yield of the title compound as a yellow-brown solid, mp 221.5°-223° C.

Mass spectrum (FAB): m/e 388 (M+ for cation).
Analysis (C₂₃H₂₆ClN₅O): Calculated: C, 65.16; H, 6.18; N, 16.51 and Found: C, 65.30; H, 6.08; N, 16.62.

¹H NMR (DMSO-d₆, 400 MHz, ppm): δ0.76 (t, 3H), 1.24 (m, 2H), 1.46 (m, 2H), 2.22 (s, 3H), 2.60 (t, 2H), 5.26 (s, 2H), 5.41 (s, 2H), 7.36 (d, 2H), 7.55–7.7 (m, 4H), 7.80 (dd, 1H), 7.96 (d, 1H), 8.94 (br s, 2H).

Step B:
2-Butyl-3-[(2'-carbamoylbiphenyl-4-yl)-methyl]-5-methyl-3H-imidazo[1,2-b][1,2,4]-triazole and 2-Butyl-3-[(2'-cyanobiphenyl-4-yl)-methyl]-5-methyl-3H-imidazo[1,2-b]-[1,2,4]triazole Reaction of 1-acetonyl-5-amino-3-butyl-4-[(2'cyanobiphenyl-4-yl)methyl]-4H-1,2,4-triazolium chloride (from Step A) with polyphosphoric acid according to the procedure of Example 2, Step B, gave a 21% yield of the nitrile, 2-butyl-3-[(2'-cyanobiphenyl-4-yl)methyl]-5-methyl-3H-imidazo[1,2-b]-[1,2,4]triazole [yellow oil; homogeneous by TLC in 19:1 CH₂Cl₂-MeOH; mass spectrum (FAB): m/e 370 (M+1)] and a 40% yield of the carboxamide, 2-butyl-3-[(2'-carbamoylbiphenyl-4-yl)methyl]-5-methyl-3H-imidazo-[1,2-b][1,2,4]triazole [very pale orange solid of indefinite mp; homogeneous by TLC in 19:1 CH₂Cl₂-MeOH; mass spectrum (FAB): m/e 388 (M+1)].

Step C:
2-Butyl-3-[(2'-cyanobiphenyl-4-yl)methyl]-5-methyl-3H-imidazo-[1,2-b][1,2,4]triazole Using the procedure of Example 2, Step C, 2-butyl-3-[(2'-carbamoylbiphenyl-4-yl)methyl]-5-3H-imidazo[1,2-b][1,2,4]triazole was converted in 49% yield to the title compound as an oil; homogeneous by TLC in 19:1 CH₂Cl₂-MeOH.

Mass spectrum (FAB): m/e 370 (M+1).
¹H NMR (CDCl₃, 400 MHz, ppm): δ0.89 (t, 3H), 1.38 (m, 2H), 1.68 (m, 2H), 2.34 (s, 3H), 2.67 (t, 2H), 5.28 (s, 2H), 7.04 (s, 1H), 7.37 (d, 2H), 7.4–7.5 (m, 2H), 7.52 (d, 2H), 7.62 (dd, 1H), 7.73 (d, 1H).

Step D:
2-Butyl-5-methyl-3-[[2'-(5-tetrazolyl)biphenyl-4-yl]methyl]-3H-imidazo[1,2-b]-[1,2,4]triazole Reaction of 2-butyl-3-[(2'-cyanobiphenyl-4-yl)methyl]-5-methyl-3H-imidazo[1,2-b][1,2,4]triazole (from Steps B and C) with trimethyltin azide according to the procedure of Example 1, Step G, gave a 31% yield of the title compound as a light brown solid, mp 124°–125° C.; homogeneous by TLC in 90:10:0.1 CH₂Cl₂-MeOH-AcOH.

Mass spectrum (FAB): m/e 413 (M+1).
Anaylsis [C₂₃H₂₄N₈.1.5 H₂O.0.75 C₄H₁₀O (ether)]: Calculated: C, 63.19; H, 6.04; N, 22.63 and Found: C, 63.58; H, 5.74; N, 22.72.

¹H NMR (CDCl₃, 400 MHz, ppm) δ0.96 (t, 3H), 1.47 (m, 2H), 1.80 (m, 2H), 2.52 (s, 3H), 2.89 (t, 2H), 5.30 (s, 2H), 7.05–7.2 (m, 5H), 7.4–7.6 (m, 3H), 7.86 (d, 1H).

¹H NMR (DMSO-d₆, 400 MHz, ppm): d 0.83 (t, 3H), 1.31 (m, 2H), 1.56 (m, 2H) 2.25 (s, 3H), 2.74 (t, 2H), 5.31 (s, 2H), 7.10 (d, 2H), 7.27 (d, 2H), 7.5–7.7 (m, 5H).

EXAMPLE 4

2-Butyl-5-ethyl-3-[[2'-(5-tetrazolyl)biphenyl-4-yl]-methyl]-3H-imidazo[1,2-b][1,2,4]triazole

Step A:
5-Amino-3-butyl-4-[(2'-cyanobiphenyl-4-yl)-methyl]-1-(2-oxo-1-butyl)-4H-1,2,4-triazolium bromide Reaction of 3-amino-5-butyl-4-[(2'-cyanobiphenyl-4-yl)methyl]-4H-1,2,4-triazole (from Example 1, Step D) with 1-bromo-2-butanone according to the procedure of Example 1, Step E, gave a quantitative yield of the title compound as a white solid, mp 221°-224° C.

Mass spectrum (FAB): m/e 402 (M+ for cation).

Analysis ($C_{24}H_{28}BrN_5O$): Calculated: C, 59.75; H, 5.85; N, 14.52 and Found: C, 59.46; H, 5.78; N, 14.40.

$^1$H NMR (DMSO-d$_6$, 200 MHz, ppm): δ0.77 (t, 3H), 1.01 (t, 3H), 1.25 (m, 2H), 1.48 (m, 2H), 2.5-2.7 (m, 4H), 5.20 (s, 2H), 5.39 (s, 2H), 7.37 (d, 2H), 7.55-7.7 (m, 4H), 7.81 (dd, 1H), 7.97 (d, 1H), 8.68 (s, 2H).

Step B:
2-Butyl-3-[(2'-carbamoylbiphenyl-4-yl)-methyl]-5-ethyl-3H-imidazo[1,2-b][1,2,4]-triazole and
2-Butyl-3-[(2'-cyanobiphenyl-4-yl)methyl]-5-ethyl-3H-imidazo[1,2-b][1,2,4]-triazole Reaction of 5-amino-3-butyl-4-[(2'-cyanobiphenyl-4-yl)methyl]-1-(2-oxo-1-butyl)-4H-1,2,4-triazolium bromide (from Step A) with polyphosphoric acid according to the procedure of Example 2, Step B, gave a 13% yield of the nitrile, 2-butyl-3-[(2'-cyanobiphenyl-4-yl)methyl]-5-ethyl-3H-imidazo[1,2-b]-[1,2,4]-triazole [yellow oil; homogeneous by TLC in 19:1 CH$_2$Cl$_2$-MeOH; mass spectrum (FAB); m/e 384 (M+1)] and a 74% yield of the carboxamide, 2-butyl-3-[(2'-carbamoylbiphenyl-4-yl)methyl]-5-ethyl-3H-imidazo[1,2-b][1,2,4]triazole [pale yellow solid of indefinite mp; homogeneous by TLC in 19:1 CH$_2$Cl$_2$-MeOH].

Step C:
2-Butyl-3-[(2'-cyanobiphenyl-4-yl)methyl]-5-ethyl-3H-imidazo[1,2-b][1,2,4]triazole Dehydration of 2-butyl-3-[(2'-carbamoylbiphenyl-4-yl)methyl]-5-ethyl-3H-imidazo[1,2-b][1,2,4]-triazole with polyphosphate ester (PPE) according to the procedure of Example 2, Step C, gave a 37% yield of the title compound as a yellow oil; homogeneous by TLC in 19:1 CH$_2$Cl$_2$-MeOH.

Mass spectrum (FAB): m/e 384 (M+1).

$^1$H NMR (CDCl$_3$, 400 MHz, ppm): δ0.88 (t, 3H), 1.27 (t, 3H), 1.37 (m, 2H), 1.67 (m, 2H), 2.6-2.75 (m, 4H), 5.27 (s, 2H), 7.03 (s, 1H), 7.36 (d, 2H), 7.4-7.5 (m, 2H), 7.51 (d, 2H), 7.62 (dd, 1H), 7.74 (d, 1H).

Step D:
2-Butyl-5-ethyl-3-[[2'-(5-tetrazolyl)biphenyl-4-yl]methyl]-3H-imidazo[1,2-b][1,2,4]-triazole Reaction of 2-butyl-3-[(2'-cyanobiphenyl-4-yl)methyl]-5-ethyl-3H-imidazo[1,2-b][1,2,4]triazole (from Steps B and C) with trimethyltin azide according to the procedure of Example 1, Step G, gave a 24% yield of the title compound as a light tan solid, mp>100° C. (gradual); homogeneous by TLC in 90:10:0.1 CH$_2$Cl$_2$-MeOH-AcOH.

Mass spectrum (FAB): m/e 427 (M+1).

Analysis [$C_{24}H_{26}N_8$.1.2H$_2$O.0.1C$_4$H$_{10}$O (ether) Calculated: C, 64.33; H, 6.50; N, 24.60 and Found: C, 64.30; H, 6.08; N, 24.22

$^1$H NMR (CDCl$_3$ 400 MHz, ppm); δ0.93 (t, 3H), 1.21 (t, 3H), 1.43 (m, 2H), 1.74 (m, 2H), 2.73 (q, 2H), 2.80 (t, 2H), 5.20 (s, 2H), 6.95-7.05 (m, 5H), 7.36 (d, 1H), 7.44 (dd, 1H), 7.51 (dd, 1H), 7.80 (d, 1H).

EXAMPLE 5

2-Butyl-5,6-dimethyl-3-[[2'-(5-tetrazolyl)biphenyl-4-yl]methyl]-3H-imidazo[1,2-b][1,2,4]triazole Step A:
5-Amino-3-butyl-4-[(2'-cyanobiphenyl-4-yl)-methyl]-1-(3-oxo-2-butyl)-4H-1,2,4-triazolium bromide Using the procedure of Example 1, Step E, 3-amino-5-butyl-4-[(2'-cyanobiphenyl-4-yl)methyl]-4H-1,2,4-triazole (from Example 1, Step D) was reacted with 3-bromo-2-butanone to give an essentially quantitative yield of the title compound as a stiff, yellow foam, suitable for use in the next step.

Mass Spectrum (FAB):m/e 402 (M+ for cation). $^1$H NMR (CDCl$_3$, 400 MHz, ppm): δ0.86 (t, 3H), 1.32 (m, 2H), 1.61 (m, 2H), 1.77 (d, 3H), 2.32 (s, 3H), 2.52 (m, 2H), 5.50 (d, 1H), 5.74 (d, 1H), 7.33 (d, 2H), 7.4-7.5 (m, 2H), 7.54 (d, 2H), 7.62 (dd, 1H), 7.73 (d, 1H), 8.83 (s, 2H).

Step B:
2-Butyl-3-[(2'-cyanobiphenyl-4-yl)methyl]-5,6-dimethyl-3H-imidazo[1,2-b][1,2,4]-triazole and
2-Butyl-3-[(2'-carbamoylbiphenyl-4-yl)methyl]-5,6-dimethyl-3H-imidazo[1,2-b][1,2,4]triazole Reaction of 5-amino-3-butyl-4-[(2'-cyanobiphenyl-4-yl)methyl]-1-(3-oxo-2-butyl)-4H-1,2,4-traizolium bromide (from Step A) with polyphosphoric acid according to the procedure of Example 2, Step B, gave a 30% yield of the nitrile, 2-butyl-3-[(2'-cyanobiphenyl-4-yl)methyl]-5,6-dimethyl-3H-imidazo[1,2-b][1,2,4]triazole, as an oil; homogeneous by TLC in 19:1 CH$_2$Cl$_2$-MeOH.

Mass spectrum (FAB):m/e 384 (M+1).

$^1$H NMR (CDCl$_3$, 200 MHz, ppm): δ0.89 (t, 3H), 1.38 (m, 2H), 1.68 (m, 2H), 2.27 (s, 3H), 2.34 (s, 3H), 2.68 (t, 2H), 5.26 (s, 2H), 7.3-7.55 (m, 6H), 7.62 (dd, 1H), 7.74 (d, 1H).

Also eluted from the column upon further elution was a 44% yield of the carboxamide, 2-butyl-3-[(2'-carbamoylbiphenyl-4-yl)methyl]-5,6-dimethyl-3H-imidazo[1,2-b][1,2,4]triazole, as an oil; homogeneous by TLC in 19:1 CH$_2$Cl$_2$-MeOH.

Mass spectrum (FAB):m/e 402 (M+1).

Step C:
2-Butyl-5,6-dimethyl-3-[[2'-(5-tetrazolyl)biphenyl-4-yl]methyl]-3H-imidazo[1,2-b][1,2,4]triazole Reaction of 2-butyl-3-[(2'-cyanobiphenyl-4-yl)methyl]-5,6-dimethyl-3H-imidazo[1,2-b][1,2,4]triazole (from Step B) with trimethyltin azide according to the procedure of Example 1, Step G, furnished a 40% yield of the title compound as a light tan solid, mp 138°-141° C.; homogeneous by TLC in 90:10:0.1 CH$_2$Cl$_2$-MeOH-AcOH.

Mass spectrum (FAB):m/e 427 (M+1).

Analysis ($C_{24}H_{26}N_8$.⅓H$_2$O.¼CH$_2$Cl$_2$): Calculated: C, 64.20; H, 6.04; N, 24.70 and Found: C, 64.32; H, 5.94; N, 24.74.

$^1$H NMR (CDCl, 400 MHz, ppm): δ0.93 (t, 3H), 1.43 (m, 2H), 1.74 (m, 2H), 2.21 (s, 3H), 2.30 (s, 3H), 2.80 (t, 2H), 5.13 (s, 2H), 6.90 (ABq, 4H), 7.30 (d, 1H), 7.39 (dd, 1H), 7.46 (dd, 1H), 7.73 (d, 1H).

EXAMPLE 6

2-Butyl-5-methyl-6-phenyl-3-[[2'-(5-tetrazolyl)biphenyl-4-yl]methyl]-3H-imidazo[1,2-b][1,2,4]triazole Step A:
5-Amino-3-butyl-4-[(2'-cyanobiphenyl-4-yl)methyl]-1-(2-oxo-1-phenylpropyl)-4H-1,2,4-triazolium bromide Reaction of 3-amino-5-butyl-4-[(2'-cyanobiphenyl-4-yl)methyl]-4H-1,2,4-triazole (from Example 1, Step D) with 1-bromo-1-phenylacetone [A. C. B. Smith and W. Wilson, J. Chem. Soc., 1342 (1955)] according to the procedure of Example 1, Step E, gave an essentially quantitiative yield of the title compound as a yellow oil, suitable for use in the next step.

Mass spectrum (FAB):m/e 464 (M+ for cation).

$^1$H NMR (CDCl$_3$, 400 MHz, ppm): δ0.82 (t, 3H), 1.28 (m, 2H), 1.56 (m, 2H), 2.19 (s, 3H), 2.47 (m, 2H), 5.42 (d, 1H), 5.61 (d, 1H), 7.25–7.75 (m, 13H), 8.61 (br s, 2H).

Step B:
2-Butyl-3-[(2'-cyanobiphenyl-4-yl)methyl]-5-methyl-6-phenyl-3H-imidazo[1,2-b][1,2,4]triazole and 2-Butyl-3-[(2'-carbamoylbiphenyl-4-yl)methyl]-5-methyl-6-phenyl-3H-imidazo[1,2-b][1,2,4]triazole Reaction of 5-amino-3-butyl-4-[(2'-cyanobiphenyl-4-yl)methyl]-1-(2-oxo-1-phenylpropyl)-4H-1,2,4-triazolium bromide (from Step A) with polyphosphoric acid according to the procedure of Example 2, Step B, provided a 45% yield of the nitrile, 2-butyl-3-[(2'-cyanobiphenyl-4-yl)methyl]-5-methyl-6-phenyl-3H-imidazo[1,2-b][1,2,4]triazole, as a dark oil; homogeneous by TLC in 19:1 CH$_2$Cl$_2$-MeOH.

Mass spectrum (FAB):m/e 446 (M+1).

$^1$H NMR (CDCl$_3$, 400 MHz, ppm): δ0.89 (t, 3H), 1.39 (m, 2H), 1.70 (m, 2H), 2.56 (s, 3H), 2.72 (t, 2H), 5.31 (s, 2H), 7.2–7.5 (m, 7H), 7.54 (d, 2H), 7.64 (dd, 1H), 7.74 (d, 1H), 7.78 (d, 2H).

Also isolated from the column upon further elution was a 48% yield of the carboxamide, 2-butyl-3-[(2'-carbamoylbiphenyl-4-yl)methyl]-5-methyl-6-phenyl-3H-imidazo[1,2-b][1,2,4]triazole, as a stiff, dark foam; homogeneous by TLC in 19:1 CH$_2$Cl$_2$-MeOH.

Mass spectrum (FAB):m/e 464 (M+1).

Step C:
2-Butyl-5-methyl-6-phenyl-3-[[2'-(5-tetrazolyl)biphenyl-4-yl]methyl]-3H-imidazo[1,2-b][1,2,4]triazole Following the procedure of Example 1, Step G, 2-butyl-3-[(2'-cyanobiphenyl-4-yl)methyl]-5-methyl-6-phenyl-3H-imidazo[1,2-b][1,2,4]triazole (from Step B) was reacted with trimethyltin azide to give a 32% yield of the title compound as a brown solid, mp>108° C. (gradual); homogeneous by TLC in 90:10:0.1 CH$_2$Cl$_2$-MeOH-AcOH.

Mass spectrum (FAB):m/e 489 (M+1).

Analysis [C$_{29}$H$_{28}$N$_8$.0.7H$_2$O.0.9C$_4$H$_{10}$O (ether)]: Calculated: C, 68.95; H, 6.80; N, 19.73 and Found: C, 68.79; H, 6.81; N, 19.68.

$^1$H NMR (CDCl$_3$, 400 MHz, ppm): δ0.95 (t, 3H), 1.45 (m, 2H), 1.77 (m, 2H), 2.54 (s, 3H), 2.84 (t, 2H), 5.24 (s, 2H), 7.06 (ABq, 4H), 7.3–7.55 (m, 6H), 7.71 (d, 2H), 7.86 (d, 1H).

EXAMPLE 7

2-Butyl-6-phenyl-3-[[2'-(5-tetrazolyl)biphenyl-4-yl]methyl]-3H-imidazo[1,2,-b][1,2,4]triazole Step A:
2-Butyl-3-[(2'-cyanobiphenyl-4-yl)methyl]-6-phenyl-3H-imidazo[1,2-b][1,2,4]triazole A mixture of 212 mg (0.640 mmole) of 3-amino-5-butyl-4-[(2'-cyanobiphenyl-4-yl)methyl]-4H-1,2,4-triazole (from Example 1, Step D), 151 mg (0.757 mmol) of α-bromophenylacetaldehyde [T. L. Jacobs and W. R. Scott, Jr., J. Am. Chem. Soc., 75, 5500 (1953)], and 2.0 ml of absolute ethanol was stirred at reflux under N$_2$ for 6 hours. The mixture was cooled and concentrated in vacuo. The residue was chromatographed on a column of silica gel (27×2.5 cm) packed in CH$_2$Cl$_2$ (elution with 1% and then 4% MeOH in CH$_2$Cl$_2$). Concentration of the appropriate pooled product fractions afforded 65.3 mg (24%) of the title compound as a yellow oil; homogeneous by TLC in 19:1 CH$_2$Cl$_2$-MeOH.

Mass spectrum (FAB):m/e 432 (M+1).

$^1$H NMR (CDCl$_3$, 400 MHz, ppm): δ0.93 (t, 3H), 1.44 (m, 2H), 1.76 (m, 2H), 2.77 (t, 2H), 5.29 (s, 2H), 7.2–7.5 (m, 8H), 7.53 (d, 2H), 7.62 (dd, 1H), 7.74 (d, 1H), 7.91 (d, 2H).

Step B:
2-Butyl-6-phenyl-3-[[2'-(5-tetrazolyl)biphenyl-4-yl]methyl]-3H-imidazo[1,2-b][1,2,4]triazole Reaction of 2-butyl-3-[(2'-cyanobiphenyl-4-yl)methyl]-6-phenyl-3H-imidazo[1,2-b][1,2,4]triazole (from Step A) with trimethyltin azide according to the procedure of Example 1, Step G, gave a 46% yield of the title compound as a light brown solid, mp>70° C. (gradual): homogeneous by TLC in 90:10:0.1 CH$_2$Cl$_2$-MeOH-AcOH.

Mass spectrum (FAB):m/e 475 (M+1).

Analysis [C$_{28}$H$_{26}$N$_8$.0.4CH$_2$Cl$_2$.C$_4$H$_{10}$O (ether)]: Calculated: C, 60.43; H, 4.53; N, 15.10 Found: C, 60.72; H, 4.51; N, 14.83.

$^1$H NMR (CDCl$_3$, 400 MHz, ppm): δ0.94 (t, 3H), 1.45 (m, 2H), 1.78 (m, 2H), 2.80 (t, 2H), 5.11 (s, 2H), 7.03 (m, 4H), 7.2–7.6 (m, 7H), 7.85 (d, 2H), 7.91 (d, 1H).

What is claimed is:
1. A compound of structural formula:

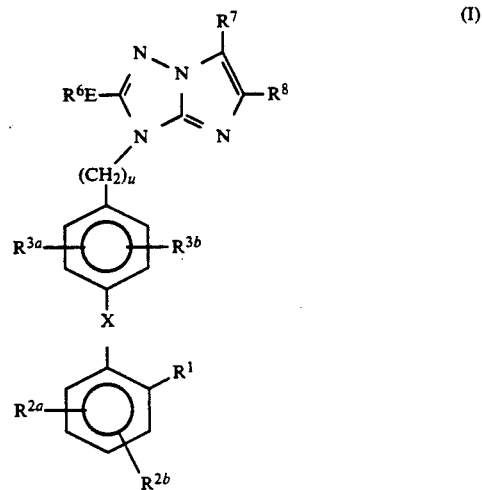

(I)

or a pharmaceutically acceptable salt thereof wherein:

$R^1$ is
- (a) —$CO_2R^5$,
- (b) —$SO_3R^5$,
- (c) —$NHSO_2CF_3$,
- (d) —$PO(OR^5)_2$,
- (e) —$SO_2$—NH—$R^9$,
- (f) —$CONHOR^5$,
- (g) —$SO_2NHCOR^{23}$,
- (h) —$CH_2SO_2NHCOR^{23}$,
- (i) —$CONHSO_2R^{23}$,
- (j) —$CH_2CONHSO_2R^{23}$,
- (k) —$NHSO_2NHCOR^{23}$,
- (l) —$NHCONHSO_2R^{23}$, (m) 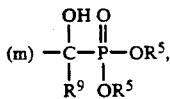

(n) 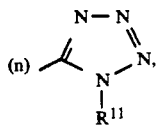

(o) 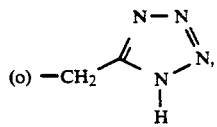

(p) 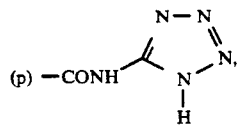

(q) —$CONHNHSO_2CF_3$, (r) 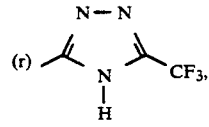

(s) 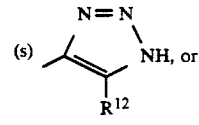

(t) 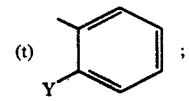;

Y is
- (1) —$CO_2R^4$,
- (2) —$SO_3R^5$,
- (3) —$NHSO_2CF_3$,
- (4) —$PO(OR^5)_2$,
- (5) —$SO_2$—NH—$R^9$, or
- (6) 1H-tetrazol-5-yl;

$R^{2a}$ and $R^{2b}$ are each independently:
- (a) hydrogen,
- (b) Cl, Br, I, F,
- (c) $NO_2$,
- (d) $NH_2$,
- (e) ($C_1$-$C_4$)-alkylamino,
- (f) —$SO_2NHR^9$,
- (g) $CF_3$,
- (h) ($C_1$-$C_4$)-alkyl
- (i) ($C_1$-$C_4$)-alkoxy, or
- (j) when $R^{2a}$ and $R^{2b}$ are on adjacent carbons, they can be bonded together to form a phenyl ring;

$R^{3a}$ is
- (a) H,
- (b) Cl, Br, I, F,
- (c) ($C_1$-$C_6$)-alkyl,
- (d) ($C_1$-$C_6$)-alkoxy,
- (e) ($C_1$-$C_6$)-alkoxy-($C_1$-$C_4$)-alkyl;

$R^{3b}$ is
- (a) H,
- (b) Cl, Br, I, F,
- (c) $NO_2$,
- (d) ($C_1$-$C_6$)-alkyl,
- (e) ($C_1$-$C_5$)-alkylcarbonyloxy,
- (f) ($C_3$-$C_6$)-cycloalkyl,
- (g) ($C_1$-$C_6$)-alkoxy,
- (h) —$NHSO_2R^4$,
- (i) hydroxy-($C_1$-$C_4$)-alkyl,
- (j) aryl-($C_1$-$C_4$)-alkyl,
- (k) ($C_1$-$C_4$)-alkylthio,
- (l) ($C_1$-$C_4$)-alkylsulfinyl,
- (m) ($C_1$-$C_4$)-alkylsulfonyl,
- (n) $NH_2$,
- (o) ($C_1$-$C_4$)-alkylamino,
- (p) di[($C_1$-$C_4$)-alkyl]amino,
- (q) $CF_3$,
- (r) —$SO_2$—$NHR^9$,
- (s) phenyl or naphthyl unsubstituted or substituted with one or two substituents selected from the group consisting of: Cl, Br, I, F ($C_1$-$C_4$)-alkyl, ($C_1$-$C_4$)-alkoxy, $NO_2$, $CF_3$, ($C_1$-$C_4$)-alkylthio, OH or $NH_2$,
- (t) furyl, or
- (u) when $R^{3a}$ and $R^{3b}$ are on adjacent carbons, they can be bonded together to form a phenyl ring;

$R^4$ is H, ($C_1$-$C_6$)-alkyl, phenyl, naphthyl, $CH_2$-phenyl or $CH_2$-naphthyl;

$R^{4a}$ is ($C_1$-$C_6$)-alkyl, phenyl, naphthyl, $CH_2$-phenyl or $CH_2$-naphthyl;

$R^5$ is H or —$CH(R^4)$—O—CO—$R^{4a}$;

E is a single bond, —$NR^{13}(CH_2)_s$—, —$S(O)_x(CH_2)_s$—where x is 0 to 2 and s is 0 to 5, —CH(OH)—, —$O(CH_2)_s$— or —CO—;

$R^6$ is
- (a) phenyl or naphthyl, unsubstituted or substituted with 1 or 2 substituents selected from the group consisting of: Cl, Br, I, F, —O—($C_1$-$C_4$)-alkyl, ($C_1$-$C_4$)-alkyl, —$NO_2$, —$CF_3$, —$SO_2NR^9R^{10}$, —S—($C_1$-$C_4$)-alkyl, —OH, —$NH_2$, ($C_3$-$C_7$)-cycloalkyl, ($C_3$-$C_{10}$)-alkenyl,
- (b) ($C_1$-$C_6$)-alkyl, ($C_2$-$C_6$)-alkenyl or ($C_2$-$C_6$)-alkynyl each of which can be unsubstituted or substituted with one or more substituents selected from the group consisting of: phenyl or naphthyl, $C_3$-$C_7$-cycloalkyl, Cl, Br, I, F, —OH, —O—$C_1$-$C_4$-alkyl, —$NH_2$, —NH(($C_1$-$C_4$)-alkyl), —N[($C_1$-$C_4$)-alkyl]$_2$, —NH—$SO_2R^4$, —$COOR^4$, —$SO_2NHR^9$, or —S—($C_1$-$C_4$)-alkyl,
- (c) mono-, di-, tri- or polyfluoro-($C_1$-$C_5$)-alkyl,
- (d) ($C_3$-$C_7$)-cycloalkyl, unsubstituted or substituted with one or more substituents selected from the group consisting of: ($C_1$-$C_4$)-alkyl, O-($C_1$-$C_4$)-alkyl, S—($C_1$-$C_4$)-alkyl, OH, perfluoro-($C_1$-$C_4$)-alkyl, Cl, Br, F or I, or (e) $(C_3-C_7)$-cycloalkyl-$(C_1-C_3)$-alkyl wherein the cycloalkyl is substituted with one or more substituents selected from the group consisting of: $(C_1-C_4)$-alkyl, O—$(C_1-C_4)$-alkyl, S—$(C_1-C_4)$-alkyl, OH, perfluoro-$(C_1-C_4)$-alkyl, Cl, Br, F or I;

$R^7$ and $R^8$ are independently:
(a) H,
(b) $(C_1-C_{10})$-alkyl, unsubstituted or substituted $(C_1-C_{10})$-alkyl in which one or more substituent(s) is selected from the group consisting of:
  (1) I, Br, Cl, F,
  (2) hydroxy,
  (3) $(C_1-C_{10})$-alkoxy,
  (4) $(C_1-C_5)$-alkoxycarbonyl,
  (5) $(C_1-C_4)$-alkylcarbonyloxy,
  (6) $(C_3-C_8)$-cycloalkyl,
  (7) phenyl or naphthyl
  (8) substituted phenyl or naphthyl in which the substituents are $V_1$, $V_2$, $V_3$, $V_4$ and $V_5$,
  (9) $(C_1-C_{10})$-alkyl-$S(O)_p$ in which p is 0 to 2,
  (10) $(C_3-C_8)$-cycloalkyl-$S(O)_p$,
  (11) phenyl-$S(O)_p$,
  (12) substituted phenyl-$S(O)_p$ in which the substituents are $V_1$-$V_5$,
  (13) oxo,
  (14) carboxy,
  (15) $NR^9R^9$,
  (16) CONH-$(C_1-C_5)$-alkyl,
  (17) CON[$(C_1-C_5)$-alkyl]$_2$, or
  (18) cyano,
(c) $(C_2-C_{10})$-alkenyl,
(d) $(C_2-C_{10})$-alkynyl,
(e) $(C_3-C_8)$-cycloalkyl,
(f) substituted $(C_3-C_8)$-cycloalkyl or substituted $(C_3-C_8)$-cycloalkyl-$C_1-C_4$-alkyl having one or more substituents selected from the group:
  (1) Cl, Br, F, I,
  (2) hydroxy,
  (3) $(C_1-C_6)$-alkyl,
  (4) $(C_1-C_6)$-alkoxy,
  (5) $(C_1-C_4)$-alkylcarbonyloxy,
  (6) $(C_1-C_5)$-alkoxycarbonyl,
  (7) carboxy,
  (8) oxo,
  (9) $(C_1-C_5)$-alkylaminocarbonyl,
  (10) di[$(C_1-C_5)$]-alkylaminocarbonyl,
  (11) $(C_1-C_4)$-alkylcarbonyl,
  (12) phenyl or naphthyl or
  (13) substituted phenyl or naphthyl in which the substituents are $V_1$, $V_2$, $V_3$, $V_4$ and $V_5$,
(g) phenyl or naphthyl
(h) substituted phenyl or naphthyl in which the substituents are $V_1$, $V_2$, $V_3$, $V_4$ and $V_5$,
(i) phenyl—$(CH_2)_r$—$(Q)_c$—$(CH_2)_t$— or naphthyl —$(CH_2)_r$—$(Q)_c$—$(CH_2)_t$—,
(j) substituted phenyl —$(CH_2)_r$—$(Q)_c$—$(CH_2)_t$— or substituted naphthyl —$(CH_2)_r$—$(Q)_c$—$(CH_2)_t$— in which the phenyl or naphthyl group is substituted with $V_1$, $V_2$, $V_3$, $V_4$ and $V_5$,
(k) a heterocyclic moiety selected from the group consisting of:

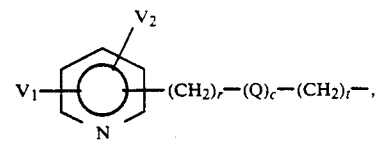

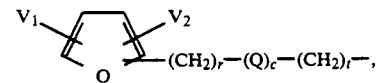

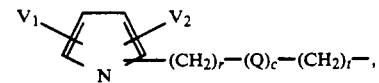

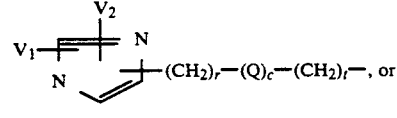

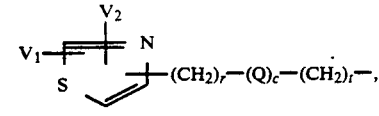

(l) Cl, Br, I, F,
(m) nitro,
(n) nitroso,
(o) $NR^9R^{10}$,
(p) $NR^4COR^9$,
(q) $NR^4CO_2R^9$,
(r) $NR^4CONR^9R^{10}$, (s) $N(R^4)CON$G (t) $NHSO_2CF_3$,
(u) $CO_2R^4$,
(v) CN,
(w) 1H-tetrazol-5-yl,
(x) O—$(C_1-C_4)$-alkyl, or
(y) $S(O)_p$—$(C_1-C_4)$-alkyl;

G is O, $S(O)_p$, or $NR^9$;

$R^9$ is H, $(C_1-C_5)$-alkyl; phenyl, naphthyl, $CH_2$-phenyl or $CH_2$-naphthyl;

$R^{10}$ is H, $(C_1-C_4)$-alkyl, or $R^9$ and $R^{10}$ together can be —$(CH_2)_m$—, where m is 3-6;

$R^{11}$ is H, $(C_1-C_6)$-alkyl, $(C_2-C_4)$-alkenyl, $(C_1-C_4)$-alkoxy-$(C_1-C_4)$-alkyl, or —$CH_2$—$C_6H_4R^{20}$;

$R^{12}$ is —CN, —$NO_2$ or —$CO_2R^4$;

$R^{13}$ is H, $(C_1-C_4)$-acyl, $(C_1-C_6)$-alkyl, allyl, $(C_3-C_6)$-cycloalkyl, phenyl or benzyl;

$R^{14}$ is H, $(C_1-C_8)$-alkyl, $(C_1-C_8)$-perfluoroalkyl, $(C_3-C_6)$-cycloalkyl, phenyl or benzyl;

$R^{15}$ is H, $(C_1-C_6)$-alkyl or hydroxy;

$R^{16}$ is H, $(C_1-C_6)$-alkyl, $(C_3-C_6)$-cycloalkyl, phenyl or benzyl;

$R^{17}$ is —$NR^9R^{10}$, —$OR^{10}$, —$NHCONH_2$, —$NHCSNH_2$, —$NHSO_2CF_3$,

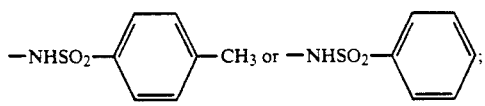

R$^{18}$ and R$^{19}$ are independently (C$_1$-C$_4$)-alkyl or taken together are —(CH$_2$)$_q$— where q is 2 or 3;

R$^{20}$ is H, —NO$_2$, —NH$_2$, —OH or —OCH$_3$;

R$^{23}$ is
(a) phenyl or naphthyl
(b) (C$_3$-C$_7$)-cycloalkyl,
(c) (C$_1$-C$_4$)-alkyl, unsubstituted or substituted with a substituent selected from the group consisting of: aryl, heteroaryl, —OH, —SH, (C$_1$-C$_4$)-alkyl, —O((C$_1$-C$_4$)-alkyl), —CH$_3$, S(C$_1$-C$_4$)-alkyl, Cl, Br, F, I, —NO$_2$, —CO$_2$H, —CO$_2$—(C$_1$-C$_4$)-alkyl, —NH$_2$, —NH(C$_1$-C$_4$)-alkyl, —N((C$_1$-C$_4$)-alkyl)$_2$, —N(CH$_2$CH$_2$)$_2$L, —PO$_3$H, or —PO(OH)(O—(C$_1$-C$_4$)-alkyl);

L is a single bond, CH$_2$, O, S(O)$_p$, or NR$^9$;

X is
(a) a single bond,
(b) —CO—,
(c) —O—,
(d) —S—,
(e) —N—, R$^{13}$
(f) —CON—, R$^{15}$
(g) —NCO—, R$^{15}$
(h) —OCH$_2$—,
(i) —CH$_2$O—
(j) —SCH$_2$—,
(k) —CH$_2$S—,
(l) —NHC(R$^9$)(R$^{10}$)—,
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—,

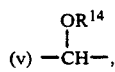
(v) —CH—,

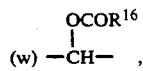
(w) —CH—,

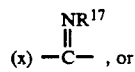
(x) —C—, or

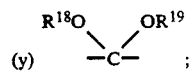
(y) ;

Q is —C(O)—, —S—, —O— or —NR$^4$;
c is 0 or 1;
r and t are 0 to 2;
V$_1$, V$_2$, V$_3$, V$_4$ and V$_5$ are each independently selected from:
(a) H,
(b) (C$_1$-C$_5$)-alkoxy,
(c) (C$_1$-C$_5$)-alkyl,
(d) hydroxy,
(e) (C$_1$-C$_5$)-alkyl-S(O)$_p$,
(f) —CN,
(g) —NO$_2$,
(h) —NR$^9$R$^{10}$,
(i) (C$_1$-C$_5$)-alkyl-CONR$^9$R$^{10}$,
(j) —CONR$^9$R$^{10}$,
(k) —CO$_2$R$^9$,
(l) (C$_1$-C$_5$)-alkyl-carbonyl,
(m) CF$_3$,
(n) I, Br, Cl, F,
(o) hydroxy-(C$_1$-C$_4$)-alkyl-,
(p) carboxy-(C$_1$-C$_4$)-alkyl-,
(q) -1H-tetrazol-5-yl,
(r) —NH—SO$_2$CF$_3$,
(s) aryl,
(t) (C$_1$-C$_5$)-alkyl-CO$_2$R$^9$,
(u) phenoxy or naphthoxy,
(v) phenyl-(C$_1$-C$_3$)-alkoxy, or naphthyl-(C$_1$-C$_3$)-alkoxy,
(w) phenyl-(C$_1$-C$_3$)-alkyl, or naphthyl-(C$_1$-C$_3$)-alkyl,
(x) carboxyphenyl,
(y) 2-oxazolin-2-yl, unsubstituted or substituted with one or more (C$_1$-C$_4$)-alkyl substituents,
(z) —(CH$_2$)$_t$OCOR$^9$,
(aa) —(CH$_2$)$_t$OCONR$^9$R$^{10}$,
(bb) —(CH$_2$)$_t$NR$^4$COR$^9$,
(cc) —(CH$_2$)$_t$NR$^4$CO$_2$R$^9$,
(dd) —(CH$_2$)$_t$NR$^4$CONR$^9$R$^{10}$,

(ee) —(CH$_2$)$_t$NR$^4$CON G,

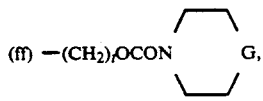
(ff) —(CH$_2$)$_t$OCON G,

(gg) —N(CH$_2$CH$_2$)$_2$G,

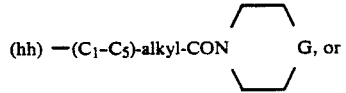
(hh) —(C$_1$-C$_5$)-alkyl-CON G, or

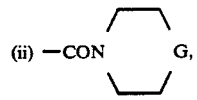
(ii) —CON G,

G is O, S(O)$_p$ or NR$^9$;
u is 1 or 2;
Z is O, NR$^{13}$ or S.

2. The compound of claim 1 or a pharmaceutically acceptable salt wherein:

R$^1$ is
(a) —CO$_2$H,
(b) -1H-tetrazol-5-yl,
(c) —NHSO$_2$CF$_3$,
(d) —CONHSO$_2$R$^{23}$, or
(e) —SO$_2$NHCOR$^{23}$;

R$^{2a}$ is H;
R$^{2b}$ is:
(a) hydrogen,
(b) Cl, F, (g) CF₃,
(h) (C₁–C₄)-alkyl,
(i) (C₁–C₄)-alkoxy;

$R^{3a}$ is H;

$R^{3b}$ is
 (a) H,
 (b) Cl, F,
 (c) (C₁–C₄)-alkyl,
 (d) CF,
 (e) (C₃–C₆)-cycloalkyl, or
 (f) (C₁–C₄)-alkoxy;

$R^4$ is H, (C₁–C₆)-alkyl, phenyl, naphthyl, CH₂-phenyl or CH₂-naphthyl;

$R^{4a}$ is (C₁–C₆)-alkyl, phenyl, naphthyl, CH₂-phenyl or CH₂-naphthyl;

$R^5$ is H or —CH($R^4$)—O—CO—$R^{4a}$;

E is a single bond or —S—;

$R^6$ is
 (a) (C₁–C₆)-alkyl, (C₂–C₆)-alkenyl or (C₂–C₆)-alkynyl each of which can be unsubstituted or substituted with one or more substituents selected from the group consisting of: aryl, C₃–C₇-cycloalkyl, Cl, Br, I, F, —OH, —O—C₁–C₄-alkyl, —COOR⁴, or —S—(C₁–C₄)-alkyl,
 (b) (C₁–C₅)-perfluoroalkyl, or
 (c) (C₃–C₇)-cycloalkyl, unsubstituted or substituted with one or more substituents selected from the group consisting of: (C₁–C₄)-alkyl, O—(C₁–C₄)-alkyl, S—(C₁–C₄)-alkyl, OH, (C₁–C₄)perfluoroalkyl, Cl, Br, F or I;

$R^7$ and $R^8$ are independently:
 (a) H,
 (b) (C₁–C₆)-alkyl, unsubstituted or substituted (C₁–C₆)-alkyl in which one or more substituent(s) is selected from the group consisting of:
  (1) hydroxy,
  (2) (C₁–C₁₀)-alkoxy,
  (3) (C₁–C₅)-alkoxycarbonyl,
  (4) (C₁–C₄)-alkylcarbonyloxy,
  (5) (C₃–C₈)-cycloalkyl,
  (6) phenyl,
  (7) substituted phenyl in which the substituents are V₁, V₂, V₃, V₄ and V₅,
  (8) (C₁–C₆)-alkyl-S(O)ₚ in which p is 0 to 2,
  (9) (C₃–C₈)-cycloalkyl-S(O)ₚ,
  (10) phenyl-S(O)ₚ,
  (11) substituted phenyl-S(O)ₚ in which the substituents are V₁–V₅,
  (12) oxo, or
  (13) carboxy;
 (c) (C₂–C₁₀)-alkenyl,
 (d) (C₂–C₁₀)-alkynyl,
 (e) (C₃–C₈)-cycloalkyl,
 (f) substituted (C₃–C₈)-cycloalkyl or substituted (C₃–C₈)-cycloalkyl-C₁–C₄-alkyl having one or more substituents selected from the group:
  (1) Cl, Br, F, I,
  (2) hydroxy,
  (3) (C₁–C₆)-alkyl,
  (4) (C₁–C₆)-alkoxy,
  (5) (C₁–C₄)-alkylcarbonyloxy,
  (6) (C₁–C₅)-alkoxycarbonyl,
  (7) carboxy,
  (8) oxo,
  (9) phenyl naphthyl or
  (10) substituted phenyl or naphthyl in which the substituents are V₁, V₂, V₃, V₄ and V₅,
 (g) phenyl or naphthyl,
 (h) substituted phenyl or naphthyl in which the substituents are V₁, V₂, V₃, V₄ and V₅,
 (i) phenyl —(CH₂)ᵣ—(Q)_c—(CH₂)ₜ—, or naphthyl—(CH₂)ᵣ—(Q)_c—(CH₂)ₜ—,
 (j) substituted phenyl—(CH₂)ᵣ—(Q)_c—(CH₂)ₜ— or naphthyl—(CH₂)ᵣ—(Q)_c—(CH₂)ₜ— in which the aryl group is substituted with V₁, V₂, V₃, V₄ and V₅,
 (k) a heterocyclic moiety selected from the group consisting of:

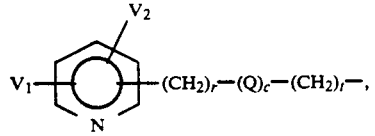
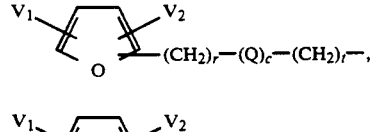
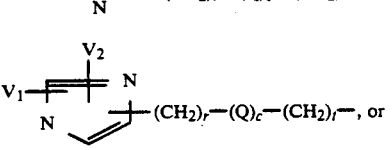
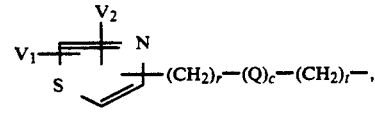

(l) Cl, Br, I, F,
 (m) CO₂R⁴,
 (n) (C₁–C₁₀)-perfluoroalkyl;

X is
 (a) a single bond,
 (b) —C(O)—, or
 (c) —NHC(O);

V₁, V₂, V₃, V₄ and V₅ are each independently selected from:
 (a) H,
 (b) (C₁–C₅)-alkoxy,
 (c) (C₁–C₅)-alkyl,
 (d) hydroxy,
 (e) (C₁–C₅)-alkyl-S(O)ₚ,
 (f) —CN,
 (g) —NO₂,
 (h) —NR⁹R¹⁰,
 (i) (C₁–C₅)-alkyl-CONR⁹R¹⁰,
 (j) —CONR⁹R¹⁰,
 (k) —CO₂R⁹,
 (l) CF₃,
 (m) I, Br, Cl, F,
 (n) hydroxy-(C₁–C₄)-alkyl-,
 (o) -1H-tetrazol-5-yl,
 (p) —NH—SO₂CF₃,
 (q) phenyl or naphthyl,
 (r) (C₁–C₅)-alkyl-CO₂R⁹,
 (s) phenyl-(C₁–C₃)-alkyl or naphthyl -(C₁–C₃)-alkyl,
 (t) 2-oxazolin-2-yl, unsubstituted or substituted with one or more (C₁–C₄)-alkyl substituents,

49

(u) —(CH$_2$)$_t$OCOR$^9$, or
(v) —(CH$_2$)$_t$OCONR$^9$R$^{10}$; and
u is 1.

3. The compound of claim 2 or a pharmaceutically acceptable salt wherein:
R$^{2a}$ and R$^{2b}$ are hydrogen;
R$^{3a}$ and R$^{3b}$ are hydrogen;
E is a single bond;
R$^6$ is
 (a) (C$_1$-C$_6$)-alkyl, (C$_2$-C$_6$)-alkenyl or (C$_2$-C$_6$)-alkynyl, which can be unsubstituted or substituted with a substituent selected from the group consisting of: cyclopropyl, CF$_3$ or —S—(C$_1$-C$_2$)-alkyl;
 (b) (C$_1$-C$_5$)-perfluoroalkyl, or
 (c) (C$_3$-C$_6$)-cycloalkyl;
R$^7$ and R$^8$ are independently:
 (a) H,
 (b) (C$_1$-C$_{10}$)-alkyl, (C$_3$-C$_8$)-cycloalkyl or (C$_3$-C$_8$)-cycloalkyl-C$_1$-C$_4$-alkyl unsubstituted or substituted with one or more substituents selected from the group consisting of:
  (1) hydroxy,
  (2) (C$_1$-C$_6$)-alkoxy,
  (3) (C$_1$-C$_5$)-alkoxycarbonyl,
  (4) carboxy,
  (5) oxo, or
  (6) phenyl, unsubstituted or substituted in which the substituents are V$_1$, V$_2$, V$_3$, V$_4$ and V$_5$;
 (c) phenyl, unsubstituted or substituted in which the substituents are V$_1$, V$_2$, V$_3$, V$_4$ and V$_5$,
 (d) phenyl—(CH$_2$)$_r$—(Q)$_c$—(CH$_2$)$_t$—, unsubstituted or substituted in which the phenyl group is substituted with V$_1$, V$_2$, V$_3$, V$_4$ and V$_5$,
 (e) a heterocyclic moiety selected from the group consisting of:

[structures with V$_1$, V$_2$ substituents on pyridine, furan, pyrrole, pyrimidine, and thiazole rings, each with —(CH$_2$)$_r$—(Q)$_c$—(CH$_2$)$_t$— linker]

(f) Cl, Br, I, F,
 (g) CO$_2$R$^4$, or
 (h) (C$_1$-C$_{10}$)-perfluoroalkyl; and
V$_1$, V$_2$, V$_3$, V$_4$ and V$_5$ are each independently selected from:
 (a) H,

50

(b) (C$_1$-C$_5$)-alkoxy,
 (c) (C$_1$-C$_5$)-alkyl,
 (d) hydroxy,
 (e) (C$_1$-C$_5$)-alkyl-S(O)$_p$,
 (f) —CN,
 (g) —NO$_2$,
 (h) —NR$^9$R$^{10}$,
 (i) (C$_1$-C$_5$)-alkyl-CONR$^9$R$^{10}$,
 (j) —CONR$^9$R$^{10}$,
 (k) —CO$_2$R$^9$,
 (l) CF$_3$,
 (m) I, Br, Cl, F,
 (n) hydroxy-(C$_1$-C$_4$)-alkyl-,
 (o) phenyl,
 (p) (C$_1$-C$_5$)-alkyl-CO$_2$R$^9$,
 (q) 2-oxazolin-2-yl, unsubstituted or substituted with one or more (C$_1$-C$_4$)-alkyl substituents,
 (r) —(CH$_2$)$_t$OCOR$^9$, or
 (s) —(CH$_2$)$_t$OCONR$^9$R$^{10}$.

4. The compound of claim 3 wherein:
E is a single bond;
R$^6$ is n-butyl, n-propyl, ethyl, or —CH$_2$SCH$_3$; and
R$^7$ and R$^8$ are independently:
 (a) H,
 (b) I, Br, Cl, F,
 (c) substituted or unsubstituted (C$_1$-C$_{10}$)-alkyl, (C$_3$-C$_8$)-cycloalkyl-(C$_1$-C$_4$)-alkyl,
 (d) phenyl, or
 (e) CO$_2$R$^9$.

5. The compound of claim 4 wherein:
R$^7$ is:
 (a) H,
 (b) I, Br, Cl, F,
 (c) (C$_1$-C$_4$)-alkyl; and
R$^{23}$ is:
 (a) phenyl,
 (b) (C$_3$-C$_7$)-cycloalkyl,
 (c) (C$_1$-C$_6$)-alkyl, or
 (d) (C$_1$-C$_4$)-perfluoroalkyl.

6. The compound of claim 1 which is a member of the group:
2-Butyl-6-methyl-5-phenyl-3-[[2'-(5-tetrazolyl)biphenyl-4-yl]methyl]-3H-imidazo[1,2-b][1,2,4]triazole;
2-Butyl-5-phenyl-3-[[2'-(5-tetrazolyl)biphenyl-4-yl]methyl]-3H-imidazo[1,2-b][1,2,4]triazole;
2-Butyl-5-methyl-3-[[2'-(5-tetrazolyl)biphenyl-4-yl]methyl]-3H-imidazo[1,2-b][1,2,4]triazole;
2-Butyl-5-ethyl-3-[[2'-(5-tetrazolyl)biphenyl-4-yl]methyl]-3H-imidazo[1,2-b][1,2,4]triazole;
2-Butyl-5,6-dimethyl-3-[[2'-(5-tetrazolyl)biphenyl-4-yl]methyl]-3H-imidazo[1,2-b][1,2,4]triazole;
2-Butyl-5-(4-methoxyphenyl)-6-methyl-3-[[2'-(5-tetrazolyl)biphenyl-4-yl]methyl]-3H-imidazo[1,2-b][1,2,4]triazole;
2-Butyl-3-[[2'-(5-tetrazolyl)biphenyl-4-yl]methyl]-3H-imidazo]1,2-b][1,2,4]triazole-5-carboxylic acid;
2-Butyl-6-methyl-3-[[2'-(5-tetrazolyl)biphenyl-4-yl]methyl]-3H-imidazo[1,2-b][1,2,4]triazole-5-carboxylic acid;
2-Butyl-5-(2-carboxyphenyl)-6-methyl-3-[[2'-(5-tetrazolyl)biphenyl-4-yl]methyl]-3H-imidazo[1,2-b][1,2,4]triazole;
5,6-Dimethyl-2-propyl-3-[[2'-(5-tetrazolyl)biphenyl-4-yl]methyl]-3H-imidazo[1,2-b][1,2,4]triazole;
5-Phenyl-2-propyl-3-[[2'-(5-tetrazolyl)biphenyl-4-yl]methyl]-3H-imidazo[1,2-b][1,2,4]triazole;
6-Methyl-5-phenyl-2-propyl-3-[[2'-(5-tetrazolyl)biphenyl-4-yl]methyl]-3H-imidazo[1,2-b][1,2,4]triazole;

6-Methyl-2-propyl-3-[[2'-(5-tetrazolyl)biphenyl-4-yl]-methyl]-3H-imidazo[1,2-b][1,2,4]triazole-5-carboxylic acid;

5,6-Dimethyl-2-ethyl-3-[[2'-(5-tetrazolyl)biphenyl-4-yl]methyl]-3H-imidazo[1,2-b][1,2,4]triazole;

2-Ethyl-5-phenyl-3-[[2'-(5-tetrazolyl)biphenyl-4-yl]-methyl]-3H-imidazo[1,2-b][1,2,4]triazole;

2-Ethyl-6-methyl-5-phenyl-3-[[2'-(5-tetrazolyl)biphenyl-4-yl]methyl]-3H-imidazo[1,2-b][1,2,4]triazole;

2-Ethyl-6-methyl-3-[[2'-(5-tetrazolyl)biphenyl-4-yl]methyl]-3H-imidazo[1,2-b][1,2,4]triazole-5-carboxylic acid;

3-[[2'-(N-Benzoylsulfamoyl)biphenyl-4-yl]methyl]-2-butyl-6-methyl-5-phenyl-3H-imidazo[1,2-b][1,2,4]triazole;

3-[[2'-(N-Benzoylsulfamoyl)biphenyl-4-yl]methyl]-2-butyl-5,6-dimethyl-3H-imidazo[1,2-b][1,2,4]triazole;

3-[[2'-(N-Benzoylsulfamoyl)biphenyl-4-yl]methyl]-6-methyl-5-phenyl-2-propyl-3H-imidazo[1,2-b][1,2,4]triazole;

3-[[2'-(N-Benzoylsulfamoyl)biphenyl-4-yl]methyl]-2-ethyl-6-methyl-5-phenyl-3H-imidazo[1,2-b][1,2,4]triazole;

2-Butyl-6-methyl-5-phenyl-3-[[2'-(trifluoromethanesulfonamido)biphenyl-4-yl]methyl]-3H-imidazo[1,2-b][1,2,4]triazole;

6-Methyl-5-phenyl-2-propyl-3-[[2'-(trifluoromethanesulfonamido)biphenyl-4-yl]methyl]-3H-imidazo[1,2-b][1,2,4]triazole;

6-Bromo-2-butyl-5-phenyl-3-[[2'-(5-tetrazolyl)biphenyl-4-yl]methyl]-3H-imidazo[1,2-b][1,2,4]triazole; or 5-Benzyl-2-butyl-6-methyl-3-[[2'-(5-tetrazolyl)biphenyl-4-yl]methyl]-3H-imidazo[1,2-b][1,2,4]triazole.

7. The compound as recited in claim 1 of structural formula:

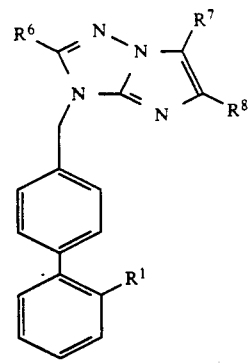

or a pharmaceutically acceptable salt, wherein:
$R^1$ is: tetrazol-5-yl, $CO_2R^5$, $SO_2NHCOR^{23}$;
$R^6$ is: n-$(C_2-C_4)$-alkyl or $CH_2SCH_3$;
$R^7$ is: H, I, Br, Cl, F, or $(C_1-C_4)$-alkyl; and
$R^8$ is H, $(C_1-C_4)$-alkyl or aryl.

8. The compound as recited in claim 4 of structural formula:

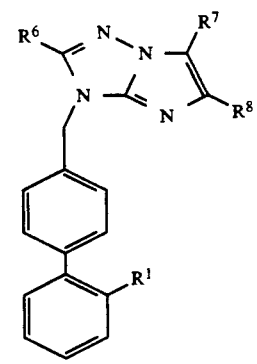

or a pharmaceutically acceptable salt, wherein:
$R^1$ is tetrazol-5-yl;
$R^6$ is n-butyl; and
$R^7$ and $R^8$ are independently: H, methyl, ethyl, or phenyl.

9. A pharmaceutical composition useful in the treatment of hypertension which comprises a pharmaceutically acceptable carrier and a pharmaceutically effective amount of a compound of claim 1.

10. A method of treating hypertension which comprises administering to a patient in need of such treatment a pharmaceutically effective amount of a compound of claim 1.

11. An ophthalmological formulation for the treatment of ocular hypertension comprising an ophthalmologically acceptable carrier and an effective ocular antihypertensive amount of a compound of claim 1.

12. A method of treating ocular hypertension comprising administering to a patient in need of such treatment an effective ocular antihypertensive amount of a compound of claim 1.

* * * * *